(12) United States Patent
He et al.

(10) Patent No.: US 7,919,634 B2
(45) Date of Patent: Apr. 5, 2011

(54) FUSED THIOPHENES, ARTICLES, AND METHODS THEREOF

(75) Inventors: Mingqian He, Horseheads, NY (US); Thomas Mark Leslie, Horseheads, NY (US); Weijun Niu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 12/473,652

(22) Filed: May 28, 2009

(65) Prior Publication Data
US 2010/0305288 A1    Dec. 2, 2010

(51) Int. Cl.
*C07D 409/00* (2006.01)
(52) U.S. Cl. ............... 549/11; 549/19; 549/20; 549/35; 526/256; 528/380
(58) Field of Classification Search .................... 528/377
See application file for complete search history.

(56) References Cited

U.S. PATENT DOCUMENTS

| | | | |
|---|---|---|---|
| 6,403,809 B1 | 6/2002 | Holmes et al. | 549/41 |
| 2007/0161776 A1 | 7/2007 | He et al. | 528/373 |
| 2007/0265418 A1 | 11/2007 | He | 528/226 |

FOREIGN PATENT DOCUMENTS

| | | | |
|---|---|---|---|
| EP | 1 275 651 B1 | | 8/2005 |
| JP | 2008-010541 | * | 1/2008 |
| WO | WO 99/12989 | | 3/1999 |
| WO | WO2006/031893 | | 3/2006 |
| WO | WO2008/106019 | | 9/2008 |

OTHER PUBLICATIONS

Gahungu et al. (Physical Chemistry Chemical Physics, 13, 2008, 1743-1747).*
He, Mingqian; Zhang, Feixia, "Synthesis and Structure of Alkyl-Substituted Fused Thiophenes Containing up to Seven Rings", Journal of Organic Chemistry (2007), 72(2), 442-451.
Fong, H. H.; Pozdin, V.A.; Amassian, A; Maliaras, G.G.; Smilgies, D; He, M; Gasper, S; Zhang, F; Sorensen, M., "Tetrathienoacene Copolymers As High Mobility, Soluble Organic Semi-conductors", Journal of the American Chemical Society (2008), 130(40), 13202-13203.
Sato, N.; Mazaki, Y.; Kobayashi, K.; Kobayashi, T., "Linearly condensed Polythiophenes: Characteristic Molecular Aggregation of Thieno[2",3":4',5']thieno[2',3'-d]thieno[3,2-b]thiophene Crystals Revealed by Ultraviolet Photoelectron Spectroscopy", Journal of the Chemical Society, Perkin Transactions 2: Physical Organic Chemistry (1972-1999) (1992), (5), 765-70.
Zhang, X.; Cote, A.P.; Matzger, A.J., "Synthesis and Structure of Fused α-Oligothiophenes with up to Seven Rings", Department of Chemistry and the Macromolecular Science and Engineering Program, University of Michigan, Ann Arbor, MI, USA. Journal of the American Chemical Society (2005), 127(30), 10502-10503.

(Continued)

*Primary Examiner* — Randy Gulakowski
*Assistant Examiner* — Shane Fang
(74) *Attorney, Agent, or Firm* — John L. Haack

(57) ABSTRACT

Fused thiophene (FT) compounds, FT polymers, FT containing articles, and methods for making and using the FT compounds and polymers thereof of the formulas, as defined herein.

8 Claims, 1 Drawing Sheet

OTHER PUBLICATIONS

Figure 1:
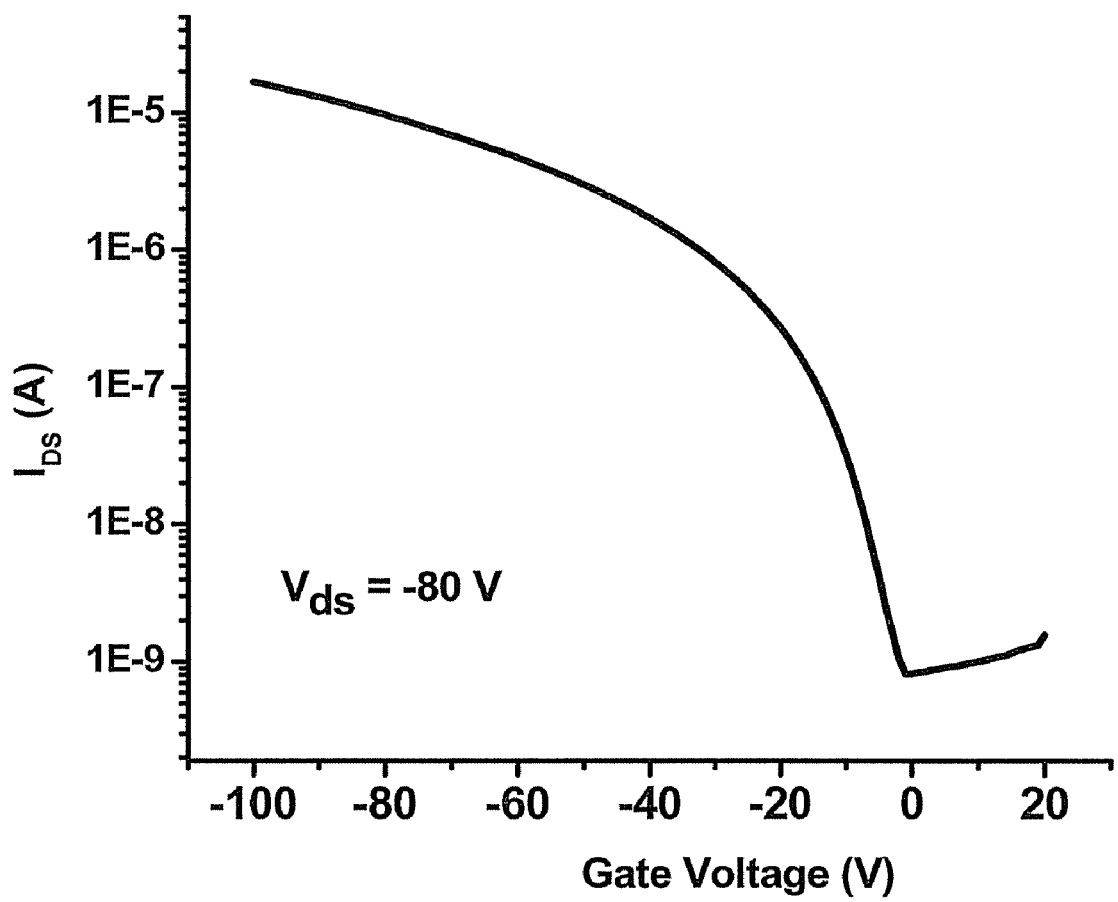

Okamoto, T.; Kudoh, K.; Wakamiya, A.; Yamaguchi, S., "General Synthesis of Extended Fused Oligothiophenes Consisting of an Even Number of Thiophene Rings", Dep. Chem., Grad. Sch. Sci., SORST, Japan Sci. Technol. Agency, Nagoya Univ., Chikusa, Nagoya, Japan. Chemistry—A European Journal (2007), 13(2), 548-556.

Anthony, John E., "Functionalized Acenes and Heteroacenes for Organic Electronics", Department of Chemistry, Univ. of Kentucky, Lexington, KY, USA. Chemical Reviews (Washington, DC, United States) (2006), 106(12), 5028-5048.

Anthony, John E, "The Larger Acenes: Versatile Organic Semiconductors", Department of Chemistry, University of Kentucky, Lexington, KY, USA, Angewandte Chemie, International Edition (2008), 47(3), 452-483.

Meng, H.; Sun, F.; Goldfinger, M. B.; Gao, F.; Londono, D. J.; Marshal, W. J.; Blackman, G. S.; Dobbs, K. D.; Keys, D. E., "2,6-Bis[2-(4-pentylphenyl)vinyl]anthracene: A Stable and High Charge Mobility Organic Semiconductor with Densely Packed Crystal Structure", Central Research and Development, Experimental Station, E. I. DuPont Company, Wilmington, DE, USA, Journal of the American Chemical Society (2006), 128(29), 9304-9305.

Klauk, H.; Zschieschang, U.; Weitz, R. T.; Meng, H.; Sun, F.; Nunes, G.; Keys, D. E.; Fincher, C.R.; Xiang, Z., "Organic Transistors Based on Di(phenylvinyl)anthracene: Performance and Stability", Max Planck Institute for Solid State Research, Stuttgart, Germany. Advanced Materials (Weinheim, Germany) (2007), 19(22), 3882-3887.

Meng, H.; Sun, F.; Goldfinger, M.B.; Jaycox, G.D.; Li, Z.; Marshall, W.J.; Blackman, G.S., "High-Performance, Stable Organic Thin-Film Field-Effect Transistors Based on Bis-5'-alkylthiophen-2'-yl-2,6-anthracene Semiconductors", Central Research and Development Experimental Station, E. I. DuPont Company, Wilmington, DE, USA., Journal of the American Chemical Society (2005), 127(8), 2406-2407.

Cicoira, F.; Santato, C.; Melucci, M.; Favaretto, L.; Gazzano, M.; Muccini, M.; Barbarella, G., "Organic Light-Emitting Transistors Based on Solution-Cast and Vacuum-Sublimed Films of a Rigid Core Thiophene Oligomer", Advanced Materials (Weinheim, Germany) (2006), 18(2), 169-174.

Sun, Y.; Ma, Y.; Liu, Y.; Lin, Y.; Wang, Z.; Wang, Y.; Di, C.; Xiao, K.; Chen, X.; Qiu, W.; Zhang, B.; Yu, G.; Hu, W.; Zhu, D., "High-performance and stable organic thin-film transistors based on fused thiophenes", Key Laboratory of Organic Solids, Institute of Chemistry, Chinese Academy of Sciences, Beijing, Peop. Rep. China. Advanced Functional Materials (2006), 16(3), 426-432.

Viola, I.; Della Sala, F.; Piacenza, M.; Favaretto, L.; Gazzano, M.; Anni, M.; Barbarella, G.; Cingolani, R.; Gigli, G., "Bicolor Pixels from a Single Active Molecular Material by Surface-Tension-Driven Deposition", Distretto tecnologico ISUFI, National Nanotechnology Laboratory (NNL) of INFM-CNR, Lecce, Italy, Advanced Materials (Weinheim, Germany) (2007), 19(12), 1597-1602.

Sun, Y.; Liu, Y.; Ma, Y.; Di, C.; Wang, Y.; Wu, W.; Yu, G.; Hu, W.; Zhu, D., "Organic thin-film transistors with high mobilities and low operating voltages based on 5,5'-bis-biphenyl-dithieno[3,2-b:2',3'-d]thiophene semiconductor and polymer gate dielectric", Applied Physics Letters (2006), 88(24), 242113/1-242113/3.

Melucci, M.; Favaretto, L.; Bettini, C.; Gazzano, M.; Camaioni, N.; Maccagnani, P.; Ostoja, P.; Monari, M.; Barbarella, G., "Liquid-Crystalline Rigid-Core Semiconductor Oligothiophenes: Influence of Molecular Structure on Phase Behaviour and Thin-Film Properties", Consiglio Nazionale Ricerche, CNR-ISOF, Bologna, Italy, Chemistry—A European Journal (2007), 13(36), 10046-10054.

Pan, H.; Li, Y.; Wu, Y.; Liu, P.; Ong, B.S.; Zhu, S.; Xu, G., "Low-Temperature, Solution-Processed, High-Mobility Polymer Semiconductors for Thin-Film Transistors", Department of Materials Science Engineering, McMaster University, ON, Can, Journal of the American Chemical Society (2007), 129(14), 4112-4113.

\* cited by examiner

FUSED THIOPHENES, ARTICLES, AND METHODS THEREOF

The entire disclosure of any publication, patent, or patent document mentioned herein is incorporated by reference.

BACKGROUND

The disclosure generally relates to fused thiophene compounds, polymers, compositions, articles, and to methods for making and using the thiophene compositions.

SUMMARY

The disclosure provides fused thiophene (FT) compounds and polymers that can be used, for example, for electronic applications, such as light emitting devices and semiconductor devices, and methods of making and using the fused thiophene products.

BRIEF DESCRIPTION OF THE DRAWING(S)

FIG. 1 provides a representative current-voltage curve for a device prepared from polymer 10, in embodiments of the disclosure.

DETAILED DESCRIPTION

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments for the claimed invention.

DEFINITIONS

"FTx" refers to fused thiophene where x is an integer indicating the number of fused thiophene ring or cycle units fused into a single core unit, for example, a FT2 has two fused rings in the core unit, a FT3 has three fused rings in the core unit, a FT4 has four fused rings in the core unit, a FT5 has five fused rings in the core unit, and like higher designations in the core unit.

"Unit," "polymerizable unit," or like terms in the context of the disclosed fused thiophene polymers refer to the number of different core units and like other conjugated units within a discrete repeat segment (n) of a polymer, see for example the core fused thiophene unit, and $G^1$ unit (note that two $G^1$ groups are present), and the $G_2$ unit in Scheme 1(d). A repeat unit can have one or more like core units and one or more additional conjugated units within a discrete repeat segment of a polymer.

"Hydrocarbon," "hydrocarbyl," "hydrocarbylene," "hydrocarbyloxy," and like terms refer to monovalent such as —R, or divalent —R— moieties, and can include, for example, alkyl hydrocarbons, aromatic or aryl hydrocarbons, alkyl substituted aryl hydrocarbons, alkoxy substituted aryl hydrocarbons, heteroalkyl hydrocarbons, heteroaromatic or heteroaryl hydrocarbons, alkyl substituted heteroaryl hydrocarbons, alkoxy substituted heteroaryl hydrocarbons, and like hydrocarbon moieties, and as illustrated herein.

"Alkyl" includes linear alkyls, branched alkyls, and cycloalkyls. "Substituted alkyl" or "optionally substituted alkyl" refers to an alkyl substituent, which can include, for example, a linear alkyl, a branched alkyl, or a cycloalkyl, having from 1 to 4 optional substituents selected from, for example, hydroxyl (—OH), halogen, amino (—NH$_2$ or —NR$_2$), nitro (—NO$_2$), acyl (—C(=O)R), alkylsulfonyl (—S(=O)$_2$R), alkoxy (—OR), and like substituents, where R is a hydrocarbyl, aryl, Het, or like moieties, such as a monovalent alkyl or a divalent alkylene having from 1 to about 10 carbon atoms. For example, a hydroxy substituted alkyl, can be a 2-hydroxy substituted propylene of the formula —CH$_2$—CH(OH)—CH$_2$—, an alkoxy substituted alkyl, can be a 2-methoxy substituted ethyl of the formula —CH$_2$—CH$_2$—O—CH$_3$, an amino substituted alkyl, can be a 1-dialkylamino substituted ethyl of the formula —CH(NR$_2$)—CH$_3$, an oligo-(oxyalkylene), poly-(oxyalkylene), or poly-(alkylene oxide) substituted alkyl, can be, for example, of the partial formula —(R—O)$_x$—, where x can be, for example, from 1 to about 50, and from 1 to about 20, and like substituted oxyalkylene substituents, such as of the formula —(CR$^5$—CHR$^5$—O)$_x$— where R$^5$ is hydrogen or a substituted or unsubstituted (C$_{1-8}$) hydrocarbyl such as alkyl, and x is an integer of from 1 to about 50.

"Aryl" includes a mono- or divalent-phenyl radical or an ortho-fused bicyclic carbocyclic radical having about nine to twenty ring atoms in which at least one ring is aromatic. Aryl (Ar) can include substituted aryls, such as a phenyl radical having from 1 to 5 substituents, for example, alkyl, alkoxy, halo, and like substituents.

"Het" includes a four-(4), five-(5), six-(6), or seven-(7) membered saturated or unsaturated heterocyclic ring having 1, 2, 3, or 4 heteroatoms selected from the group consisting of oxy, thio, sulfinyl, sulfonyl, selenium, tellurium, and nitrogen, which ring is optionally fused to a benzene ring. Het also includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxy, thio, and N(X) wherein X is absent or is H, O, (C$_{1-4}$)alkyl, phenyl, or benzyl, and a radical of an ortho-fused bicyclic heterocycle of about eight to ten ring atoms derived therefrom, particularly a benzo-derivative or one derived by fusing a propylene, trimethylene, or tetramethylene diradical thereto.

In embodiments, halo or halide includes fluoro, chloro, bromo, or iodo. Alkyl, alkoxy, etc., include both straight and branched groups; but reference to an individual radical such as "propyl" embraces only the straight chain radical, a branched chain isomer such as "isopropyl" being specifically referred to.

The carbon atom content of various hydrocarbon-containing (i.e., hydrocarbyl) moieties can alternatively be indicated by a prefix designating a lower and upper number of carbon atoms in the moiety, i.e., the prefix C$_{i-j}$ indicates a moiety of the integer "i" to the integer "j" carbon atoms, inclusive. Thus, for example, (C$_1$-C$_8$)alkyl or C$_{1-8}$alkyl refers to an alkyl of one to eight carbon atoms, inclusive, and hydrocarbyloxy such as (C$_1$-C$_8$)alkoxy or C$_{1-8}$alkoxy refers to an alkoxy radical (—OR) having an alkyl group of one to eight carbon atoms, inclusive.

Specifically, C$_{1-8}$alkyl can be, for example, methyl, ethyl, propyl, isopropyl, butyl, iso-butyl, sec-butyl, tert-butyl, pentyl, 3-pentyl, hexyl, heptyl, or octyl; (C$_{3-12}$)cycloalkyl can be cyclopropyl, cyclobutyl, cyclopentyl, cyclohexyl, cycloheptyl, cyclooctyl, including bicyclic, tricyclic, or multi-cyclic substituents, and like substituents.

A specific "hydrocarbyl" can be, for example, (C$_{1-24}$)hydrocarbyl, including all intermediate chain lengths and values.

$C_{1-8}$alkoxy can be, for example, methoxy, ethoxy, propoxy, isopropoxy, butoxy, iso-butoxy, sec-butoxy, pentoxy, 3-pentoxy, hexyloxy, 1-methylhexyloxy, heptyloxy, octyloxy, and like substituents.

H—C(=O)($C_{3-7}$)alkyl- or —($C_{2-7}$)alkanoyl can be, for example, acetyl, propanoyl, butanoyl, pentanoyl, 4-methylpentanoyl, hexanoyl, or heptanoyl. Aryl (Ar) can be, for example, phenyl, naphthyl, anthracenyl, phenanthrenyl, fluorenyl, tetrahydronaphthyl, or indanyl. Het can be, for example, pyrrolidinyl, piperidinyl, morpholinyl, thiomorpholinyl, or heteroaryl. Heteroaryl can be, for example, furyl, imidazolyl, triazolyl, triazinyl, oxazoyl, isoxazolyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for Het includes a five-(5), six-(6), or seven-(7) membered saturated or unsaturated ring containing 1, 2, 3, or 4 heteroatoms, for example, non-peroxide oxy, thio, sulfinyl, sulfonyl, selenium, tellurium, and nitrogen; and a radical of an ortho-fused bicyclic heterocycle of about eight to twelve ring atoms derived therefrom, particularly a benzo-derivative or one derived by fusing a propylene, trimethylene, tetramethylene, or another monocyclic Het diradical thereto.

Other conditions suitable for formation and modification of the compounds, oligomers, polymers, composites or like products of the disclosure, from a variety of starting materials or intermediates, as disclosed and illustrated herein are available. For example, see Feiser and Feiser, "Reagents for Organic Synthesis", Vol. 1, et seq., 1967; March, J. "Advanced Organic Chemistry," John Wiley & Sons, 4th ed. 1992; House, H. O., "Modern Synthetic Reactions," $2^{nd}$ ed., W. A. Benjamin, New York, 1972; and Larock, R. C., "Comprehensive Organic Transformations," $2^{nd}$ ed., 1999, Wiley-VCH Publishers, New York. The starting materials employed in the preparative methods described herein are, for example, commercially available, have been reported in the scientific literature, or can be prepared from readily available starting materials using procedures known in the field. It may be desirable to optionally use a protecting group during all or portions of the above described or alternative preparative procedures. Such protecting groups and methods for their introduction and removal are known in the art. See Greene, T. W.; Wutz, P. G. M. "Protecting Groups In Organic Synthesis," $2^{nd}$ ed., 1991, New York, John Wiley & Sons, Inc.

"Include," "includes," or like terms means encompassing but not limited to, that is, inclusive and not exclusive.

"Monomer," "mer," or like terms refer to a compound that can be (or has already been) covalently combined or linked with other monomers of like or different structure to form homogenous (homopolymers) or heterogenous (e.g., copolymers, terpolymers, and like heteropolymers) chains of the target polymer. Suitable monomers as disclosed and illustrated herein can include, for example, low molecular weight polymerizable compounds, such as from about 50 to about 200 Daltons, and higher molecular weight compounds, such as from about 200 to about 10,000 Daltons, including unsaturated oligomeric or unsaturated polymeric compounds.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example: through typical measuring and handling procedures used for making compounds, compositions, composites, concentrates or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. The claims appended hereto include equivalents of these "about" quantities.

"Consisting essentially of" in embodiments refers, for example, to a compound, to a polymer composition, to a method of making or using the compound, the polymer, formulation, or composition, and articles, devices, or any apparatus of the disclosure, and can include the components or steps listed in the claim, plus other components or steps that do not materially affect the basic and novel properties of the compositions, articles, apparatus, or methods of making and use of the disclosure, such as particular reactants, particular additives or ingredients, a particular agent, a particular surface modifier or condition, or like structure, material, or process variable selected. Items that may materially affect the basic properties of the components or steps of the disclosure or that may impart undesirable characteristics to the present disclosure include, for example, premature polymer chain termination, excessive crosslinking, extended or unnecessary exposure of the resulting polymer to excessively high temperatures, and like contrary steps.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

Specific and preferred values disclosed for components, ingredients, additives, initiators, metal catalysts, cross linkers, and like aspects, and ranges thereof, are for illustration only; they do not exclude other defined values or other values within defined ranges. The compositions and methods of the disclosure include those having any value or any combination of the values, specific values, more specific values, and preferred values described herein.

In embodiments, the disclosure provides FT compounds, FT polymer compositions, FT containing articles, and methods for making and using the FT compounds and the FT polymers.

In embodiments, the disclosure provides an FT compound and a method of making an FT compound as defined herein.

In embodiments, the disclosure provides an FT polymer and a method of making an FT polymer as defined herein.

In embodiments, the disclosure provides an FT polymeric composition and FT articles thereof prepared by any of the processes as defined herein.

In embodiments, the disclosure provides a polymer article prepared by one or more of the processes as defined herein.

In embodiments, the disclosure provides an article or device incorporating the polymer or polymer article as defined herein. The disclosed compositions, articles, and methods can be used to prepare many different electro-optical devices, for example, OLEDs, OFETs, OTFTs, and like devices as disclosed, for example, in *J. Am. Chem. Soc.*, 2008, 130, 13202-13203.

In embodiments, the disclosure provides a compound of the formula:

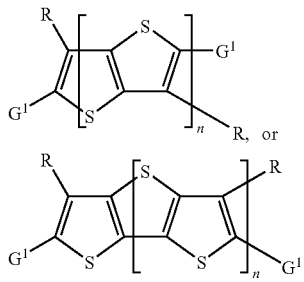

where
each R is independently a carbon-carbon bond, a carbon-sulfur bond, for example, when n is from 2 to 4, or a substituted or unsubstituted, $(C_{1-24})$hydrocarbyl including solubility enhancing substituents, for example, oxygen or sulfur substituted —R substituents such as —OR, —SR, polyethers, polythioethers, and like groups;
n is an integer from 2 to 4; and
each -$G^1$ is independently
a carbon-carbon bond or a carbon-sulfur bond, for example, when n is from 2 to 4;
a monovalent, substituted or unsubstituted, aryl of the formula —{Ar($R^1$)$_q$}$_p$—Ar($R^1$)$_q$,
a monovalent, substituted or unsubstituted, heteroaryl of the formula -{Het($R^1$)$_q$}$_p$-Het($R^1$)$_q$, or
a monovalent combination of one or more, substituted or unsubstituted, aryl and heteroaryl substituents, of the formulas —{Ar($R^1$)$_q$}$_p$-Het($R^1$)$_q$, or -{Het($R^1$)$_q$}$_p$—Ar($R^1$)$_q$, such as -Het-Ar, —Ar-Het, -Het($R^1$)$_q$—Ar, —Ar-Het($R^1$)$_q$, -Het($R^1$)$_q$—Ar($R^1$)$_q$, and like combinations,
p is 0 to 4,
q is 0 to 4, and
each —$R^1$ is independently —H, —F, or a monovalent, substituted or unsubstituted, saturated or unsaturated, $(C_{1-24})$ hydrocarbyl, or a combination thereof, and salts thereof.

Examples of —{Ar($R^1$)$_q$}$_p$—Ar($R^1$)$_q$ include, for example, —Ar($R^1$) where p is 0 and q is 1, such as —Ar, or —Ar($R^1$), —Ar($R^1$)—Ar($R^1$)— where p is 1 and q is 1 and $R^1$ is alkyl, or —Ar—Ar—Ar, where p is 2 and q is 0 and $R^1$ is —H and like permutations. Examples of -{Het($R^1$)}$_p$-Het($R^1$) include, for example, -Het, -Het-Het, -(Het)-2-Het, -Het($R^1$), -Het($R^1$)-Het, -Het-Het(R), -Het($R^1$)-Het-($R^1$), and like permutations, including, for example, phenyl, toluoyl, naphthyl, biphenyl, bithiophene, and like moieties. Examples of $(C_{1-24})$hydrocarbyl include, for example, substituted or unsubstituted, saturated or unsaturated hydrocarbyls, such as alkynyl, alkenyl, alkylenyl, or a combination thereof.

-$G^1$ combinations can include, for example, —Ar-Het, -Het-Ar, —Ar($R^1$)-Het($R^1$), -Het($R^1$)—Ar($R^1$); and like permutations of —{Ar($R^1$)$_q$}$_p$-Het(R)$_q$, or -{Het($R^1$)$_q$}$_p$—Ar($R^1$)$_q$, and salts thereof.

Specific examples of the monovalent -$G^1$ moiety can be, for example, at least one substituent selected from

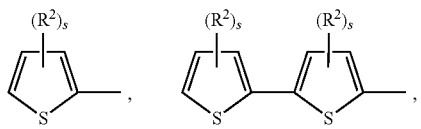

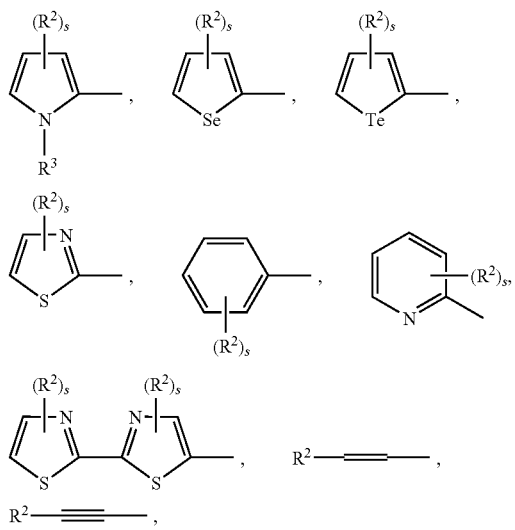

or a combination thereof,
each $R^2$ is independently H, or a monovalent, substituted or unsubstituted, saturated or unsaturated, $(C_{1-24})$hydrocarbyl, or —Ar, —F, or a combination thereof,
$R^3$ is H, or a monovalent, substituted or unsubstituted, saturated or unsaturated, $(C_{1-24})$hydrocarbyl, and
s is an integer from 0 to 5.

Examples of $R^2$ can be any of —$(C_{1-24})$hydrocarbyl, —$(C_{1-10})$alkoxyl, —{$(C_{1-10})$alkoxyl}$_t$-H, -oxyalkylene, -(oxyhydrocarbylene)$_t$H, —Ar, and like substituents, where t is from 1 to 10.

In embodiments, the disclosure provides a compound of the formula:

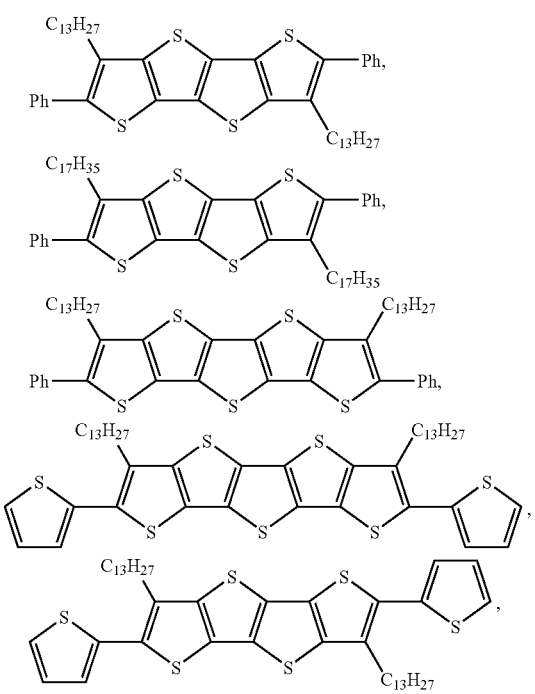

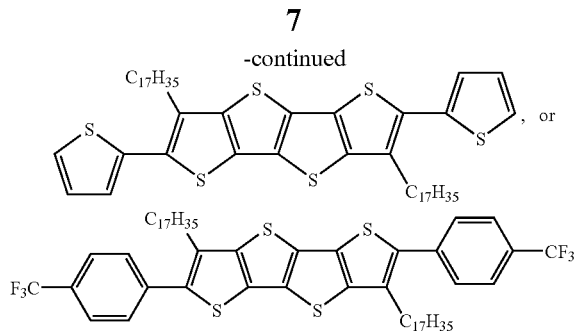

including a salt thereof, or a combination thereof, or a mixture thereof.

Specific named compounds can include, for example, 4,11-bis(thiophen-2-yl)-5,12-ditridecyl-3,7,10,14-tetrathiatetracyclo[6.6.0.0$^{2,6}$.0$^{9,13}$]tetradeca-1(8),2(6),4,9(13), 11-pentaene;

4,11-bis(thiophen-2-yl)-5,12-diheptadecyl-3,7,10,14-tetrathiatetracyclo[6.6.0.0$^{2,6}$.0$^{9,13}$]tetradeca-1(8),2(6),4,9 (13), 11-pentaene;

6,14-bis(thiophen-2-yl)-5,15-ditridecyl-3,7,10,13,17-pentathiapentacyclo[9.6.0.0$^{2,9}$.0$^{4,8}$.0$^{12,16}$]heptadeca-1(11),2 (9),4(8),5,12(16),14-hexaene;

4,11-diphenyl-5,12-ditridecyl-3,7,10,14-tetrathiatetracyclo [6.6.0.0$^{2,6}$.0$^{9,13}$]tetradeca-1(8),2(6),4,9(13), 11-pentaene;

6,14-diphenyl-5,15-ditridecyl-3,7,10,13,17-pentathiapentacyclo[9.6.0.0$^{2,9}$.0$^{4,8}$.0$^{12,16}$]heptadeca-1(11),2(9),4(8),5, 12(16),14-hexaene;

4,11-bis(4-trifluoromethylphenyl)-5,12-diheptadecyl-3,7, 10,14-tetrathiatetracyclo[6.6.0.0$^{2,6}$.0$^{9,13}$]tetradeca-1(8),2 (6),4,9(13),11-pentaene; or 4,11-diphenyl-5,12-diheptadecyl-3,7,10,14-tetrathiatetracyclo[6.6.0.0$^{2,6}$.0$^{9,13}$]tetradeca-1(8),2(6),4,9(13), 11-pentaene; and a salt thereof, or a mixture thereof.

In embodiments, -G$^1$ can be any monovalent moiety selected from, for example,

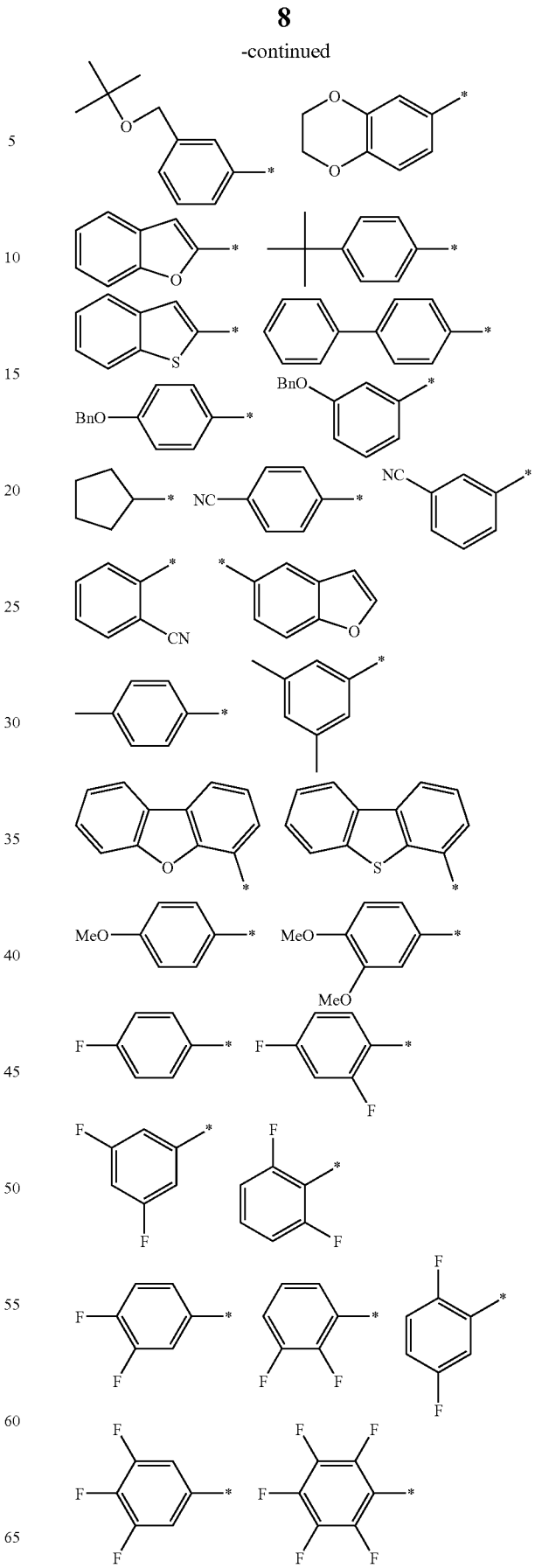

-continued

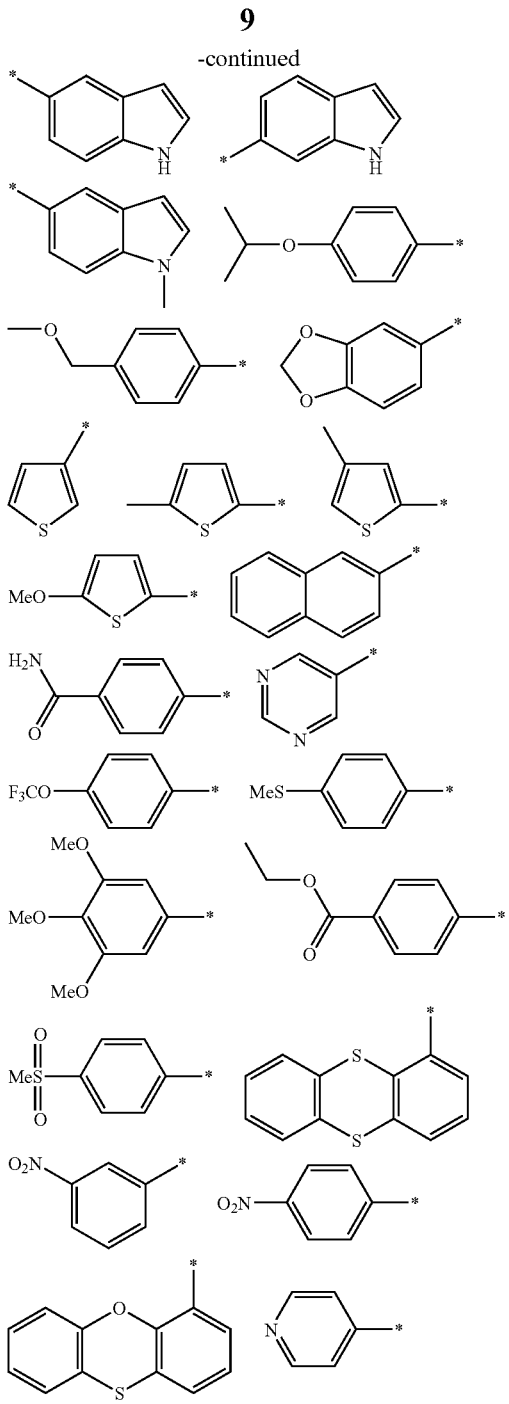

and isomeric permutations thereof, and where the asterisk "*" in the substituents represents the monovalent attachment point to the fused thiophene core.

In embodiments, the disclosure provides a method for making a fused thiophene compound of the formula:

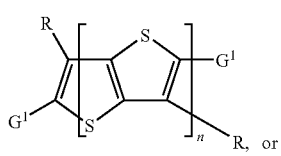

-continued

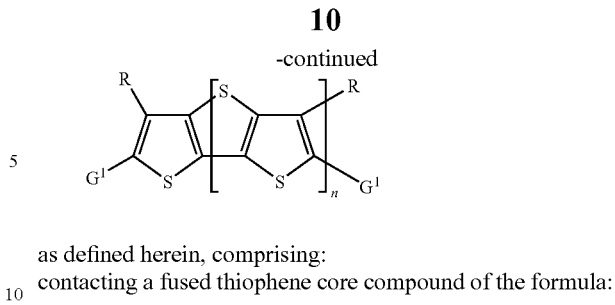

as defined herein, comprising:

contacting a fused thiophene core compound of the formula:

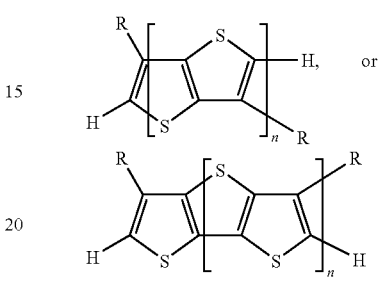

with an halogenating agent to form the α-, α'-, dihalogenated product of the formula X—C—X where X is halogen, and C is the contacted core compound; and contacting the X—C—X product with at least two mole equivalent of a coupling compound of the formula M-G$^1$ and a metal catalyst to form the α-, α'-, disubstituted product of the formula G$^1$-C-G$^1$.

More specifically the method of making can have a coupling compound of the formula M-G$^1$ which can include, for example, an M having an —SnR$^4{}_3$, —B(OH)$_2$, —B(OR$^4$)$_2$, —B(cyclo-OR$^4$O—), or —MgX, or a combination thereof, where X is halo, each R$^4$ independently is a monovalent; substituted or unsubstituted, (C$_{1-24}$)hydrocarbyl, and -G$^1$ is a monovalent moiety that can be selected from, for example,

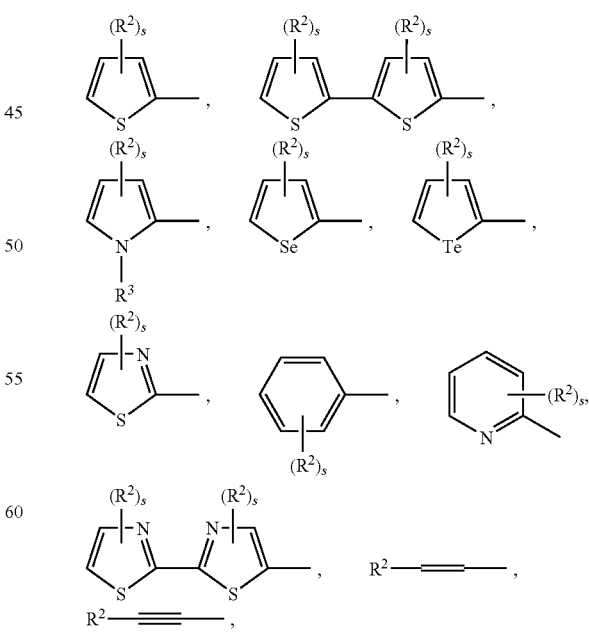

or a combination thereof, each $R^2$ is independently H, or a monovalent, substituted or unsubstituted, saturated or unsaturated, $(C_{1-24})$hydrocarbyl, —Ar, —F, and like substituents as defined herein, or a combination thereof, $R^3$ is H, or a monovalent, substituted or unsubstituted, saturated or unsaturated, $(C_{1-24})$hydrocarbyl, and s is an integer from 0 to 5.

A halogenating agent can be, for example, a brominating agent such as NBS, $Br_2$, a chlorinating agent such as NCS, $Cl_2$, an iodinating agent such as NIS, $I_2$, and like agents, or combinations thereof.

The metal catalyst can be, for example, $Pd(PPh_3)_4$, or like agents such as based on Pt, Ni, or like metals.

In embodiments, the disclosure provides a polymer of the formula:

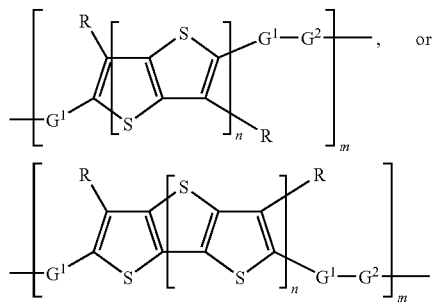

where
each R is independently a carbon-carbon bond, a carbon-sulfur bond, or a substituted or unsubstituted, $(C_{1-24})$hydrocarbyl;

n is an integer from 2 to 4;

m is an integer from 2 to 10,000, including intermediate values and ranges; and each $G^1$ is independently
a carbon-carbon bond or a carbon-sulfur bond,
a divalent, substituted or unsubstituted, aryl of the formula —{Ar($R^1$)$_q$}$_p$—Ar($R^1$)$_q$—, or
a divalent, substituted or unsubstituted, heteroaryl of the formula -{Het($R^1$)$_q$}$_p$-Het($R^1$)$_q$—, each —$R^1$ is independently —H, —F, or a monovalent, substituted or unsubstituted, saturated or unsaturated, $(C_{1-24})$hydrocarbyl, or a combination thereof, and salts thereof, each $G^2$ is independently
a divalent, substituted or unsubstituted, aryl of the formula —{Ar($R^1$)$_q$}$_p$—Ar($R^1$)$_q$—,
a divalent, substituted or unsubstituted, heteroaryl of the formula -{Het($R^1$)$_q$}$_p$-Het($R^1$)$_q$—, or
a divalent, substituted or unsubstituted, unsaturated $(C_{1-24})$ hydrocarbyl, such as a vinyl or acetylenyl, each p is independently from 0 to 4, each q is independently from 0 to 4, and each —$R^1$ is independently —H, —F, or a monovalent, substituted or unsubstituted, saturated or unsaturated, $(C_{1-24})$ hydrocarbyl, or a combination thereof, and a salt thereof.

In embodiments, the disclosed polymers can have a molecular weight, for example, of about 300 to about 25,000 or more.

In embodiments, the disclosure provides a method for making the polymer of the formulas:

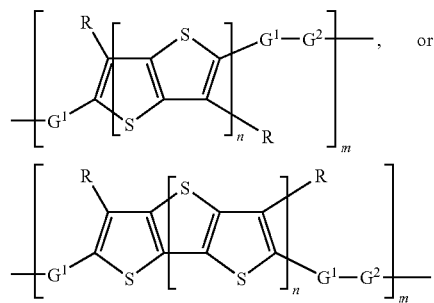

as defined here, comprising:
contacting a core compound (C) of the formula:

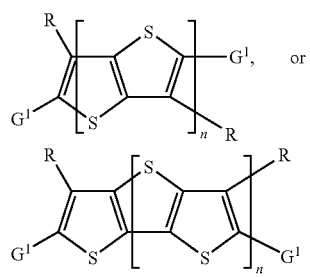

with an halogenating agent to form the α-, α'-, dihalogenated product of the formula $X-G^1-C-G^1-X$ where C is the contacted core compound and X is halogen; and contacting the $X-G^1-C-G^1-X$ product with about one mole equivalent ratio of a coupling compound of the formula $M-G^2-M$ and a metal catalyst to form the polymer.

In the preparative method to form the polymer, $M-G^2-M$ can be, for example, a coupling compound, for example, of the formula $R^4_3Sn-G^2-SnR^4_3$ using Stille coupling conditions; $(HO)_2B-G^2-B(OH)_2$, $(R^4O)_2B-G^2-B(OR^1)_2$, (cyclo-$OR^4O$—)B-$G^2$-B(cyclo —$OR^4O$—), or like metal coupling compounds using Suzuki coupling conditions; $XMg-G^2$-MgX, using Grignard coupling conditions, and like conditions, or combinations thereof, where $R^4$ can independently be a monovalent or divalent $(C_{1-8})$hydrocarbyl such as alkyl, alkylene, alkyne, including branched and cyclic hydrocarbyls such as cyclo$(C_{3-8})$alkyl, or divalent $(C_{1-8})$hydrocarbyls including cyclic glycol ethers, such as —B(cyclo-$OR^4O$—), and like substituents, where X is halogen, and -$G^2$- can be a divalent moiety of the formula, for example,

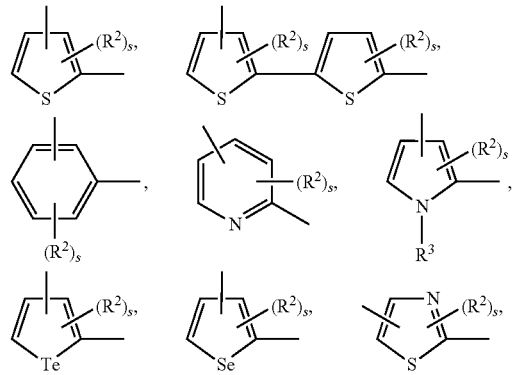

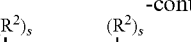

or a combination thereof,
each $R^2$ is independently H, or a monovalent, substituted or unsubstituted, saturated or unsaturated, $(C_{1-24})$hydrocarbyl, —Ar, —F, and like substituents as defined herein or a combination thereof,
$R^3$ is H, or a monovalent, substituted or unsubstituted, saturated or unsaturated, $(C_{1-24})$hydrocarbyl,
s is an integer from 0 to 5, and the metal catalyst is $Pd(PPh_3)_4$.

In embodiments the disclosure provides a method for making a polymer, comprising:
contacting a core compound of the formula:

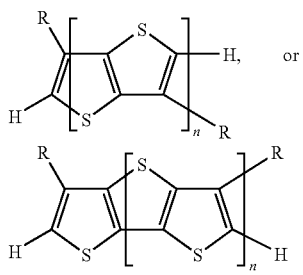

with a halogenating agent to form the α-, α'-, dihalo product of the formula X—C—X where C is the contacted core compound and X is halo; and
contacting the X—C—X product with about one mole ratio equivalent, for example, of from about 0.8 to about 1.2 mole ratio equivalents, of from about 0.9 to about 1.1 mole ratio equivalents, and preferably of from about 1.0 mole ratio equivalent, that is a 1:1 molar or mole ratio equivalents, of a coupling compound of the formula M-$G^1$-$G^2$-$G^1$-M, and a metal catalyst to form the respective polymer products of the formulas:

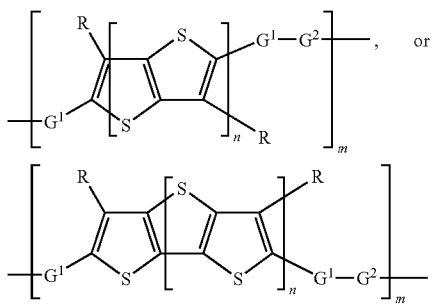

where each R is independently a monovalent, substituted or unsubstituted, $(C_{1-24})$hydrocarbyl, n is an integer from 2 to 4, and m is an integer from 2 to 10,000.

In embodiments, the coupling compound M-$G_1$-$G^2$-$G^1$-M comprises: an M having at least one —$SnR^4_3$, —$B(OH)_2$, —$B(OR^4)_2$, —$B(cyclo-OR^4O—)$, or —MgX, or a combination thereof, and each $R^4$ of the coupling compound can independently be a monovalent, substituted or unsubstituted, $(C_{1-24})$hydrocarbyl, and
each $G^1$ and $G^2$ is independently a divalent moiety selected, for example, from

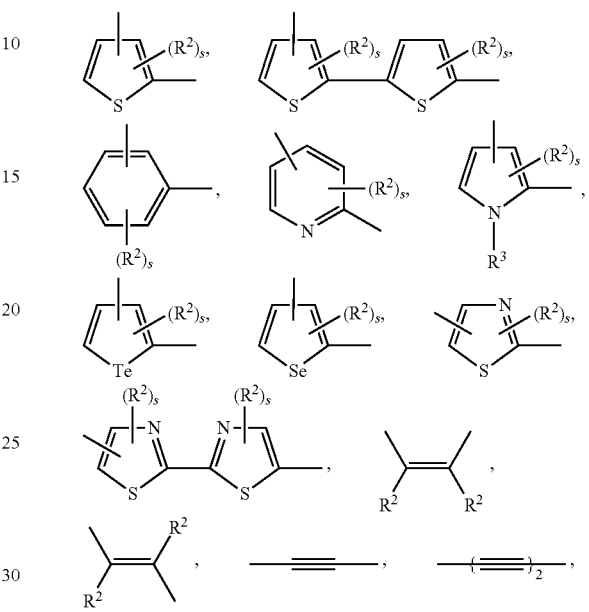

or a combination thereof,
each $R^2$ is independently H, or a monovalent, substituted or unsubstituted, saturated or unsaturated, $(C_{1-24})$hydrocarbyl, —Ar, —F, and like substituents as defined herein or a combination thereof,
$R^3$ is H, or a monovalent, substituted or unsubstituted, saturated or unsaturated, $(C_{1-24})$hydrocarbyl,
s is an integer from 0 to 5, and the metal catalyst is $Pd(PPh_3)_4$.

In embodiments, the dihalogenated compound can be, for example, of the formula

X-$G^1$-C-$G^1$-X where
C is a divalent fused thiophene core of the formula:

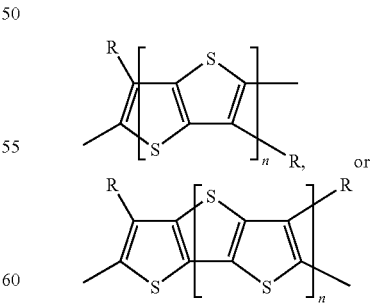

each -$G^1$- is independently:
a divalent, substituted or unsubstituted, aryl of the formula
—{Ar($R^1$)$_q$}$_p$—Ar($R^1$)$_q$—, or
a divalent, substituted or unsubstituted, heteroaryl of the formula -{Het($R^1$)$_q$}$_p$-Het($R^1$)$_q$—, each —$R^1$ is independently —H, —F, or a monovalent, substituted or unsubstituted, saturated or unsaturated, ($C_{1-24}$) hydrocarbyl, or a combination thereof, and salts thereof, each p is independently from 0 to 4,
each q is independently from 0 to 4, and
each X is independently halo, or a salt thereof, or mixtures thereof.

Specific dihalogenated compounds of the formula X-$G^1$-C-$G^1$-X can be, for example, of the formulas (7) and (9):

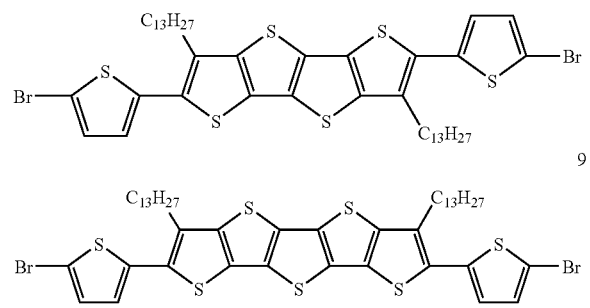

having the corresponding chemical name of:
4,11-bis(5-bromothiophen-2-yl)-5,12-ditridecyl-3,7,10,14-tetrathiatetracyclo[6.6.0.0$^{2,6}$.0$^{9,13}$]tetradeca-1(8),2(6),4,9 (13),11-pentaene (7); and
6,14-bis(5bromothiophen-2-yl)-5,15-ditridecyl-3,7,10,13, 17-pentathiapentacyclo[9.6.0.0$^{2,9}$.0$^{4,8}$.0$^{12,16}$]heptadeca-1 (11),2(9),4(8),5,12(16),14-hexaene (9).

He, M., et al., have previously reported several synthetic methods for making β-, β'-alkyl substituted fused thiophenes from FT2 to FT7 (see He, M., Int. Appl. PCT/US08/02033, PCT Publication No. WO08/106,019, U.S. Pat. Appl. Publ. US-2007-0161776 A1, a cont.-in-part of Appln. No. PCT/US2005/032759, entitled "Fused Thiophenes, Methods for Making Fused Thiophenes, and Uses Thereof"; He, M., et al., *J. Org. Chem.* (2007), 72(2), 442-451, Synthesis and Structure of Alkyl-Substituted Fused Thiophenes Containing up to Seven Rings; and commonly owned and assigned PCT Int. Appl. PCT/US05/32759, PCT Pub. No. WO06/031893, entitled "Preparation of Fused Thiophenes").

Related α-, α'-, β-, β'-unsubstituted fused thiophenes have been reported elsewhere (see for example, Fong, H. et al., *J. Am. Chem. Soc.*, (2008), 130(40), 13202-13203, Tetrathienoacene Copolymers As High Mobility, Soluble Organic Semiconductors; Zhang, X., et al., *J. Am. Chem. Soc.* (2005), 127(30), 10502-10503, Synthesis and Structure of Fused-Oligothiophenes with up to Seven Rings; Okamoto, T., et al., *Chemistry—A European Journal* (2007), 13(2), 548-556, General Synthesis of Extended Fused Oligo-Thiophenes Consisting of an Even Number of Thiophene Rings).

In embodiments, the disclosure provides α-, α'-substituted, β-, β'-alkyl substituted fused thiophene compounds (e.g., FT4, FT5, FT6, FT7, FT8, and FT9) and methods for making the compounds. Several of the β-, β'-alkyl substituted fused thiophene compounds, such as those having α-, α'-conjugated functional group substituents, can be used as organic semiconductors in electronic devices.

In embodiments, the disclosure also provides fused thiophene core compounds and their corresponding polymers having one or more additional mer units included or appended to the core. In embodiments, the additional appended unit or units can participate in polymerization and chain extension.

The resulting product can be a polymer having a repeat segment (n) including, for example, at least one core unit (C) having four or more fused thiophene rings, at least one $G^1$ unit, and at least one $G^2$ unit.

In embodiments, the resulting product can be a polymer having a repeat segment including, for example, a single fused thiophene core unit, at least two $G^1$ units, and a single $G^2$ unit. In embodiments, the disclosure provides a method for preparing polymers and block copolymers having chain segments containing, for example, from about 4 to about 10 fused thiophene units. In embodiments, the disclosure provides a method for preparing fused thiophene containing polymers and block copolymers using, for example, Stille or Suzuki coupling reactions.

In embodiments, the disclosure provides β-, β'-alkyl substituted fused thiophenes that have improved solubility in common organic solvents compared to previously reported α-, α'-, β-, β'-unsubstituted fused thiophenes. The excellent solubility property makes these materials and their conjugated polymer products suitable for solution processed organic electronics, particularly for printing applications (see PCT Appl. (not yet filed), USSN provisional patent application No. 61/072,468, assigned to Corning, Inc., filed Mar. 31, 2008, entitled "Fused Thiophenes and Methods for Making and Using Same"; Fong, H. et al., Tetrathienoacene Copolymers As High Mobility, Soluble Organic Semiconductors, *J. Am. Chem. Soc.*, (2008), 130(40), 13202-13203). The disclosed thiophenes also exhibit excellent thermal stability and air stability compared to, for example, pentacene, which rapidly decomposes in solution and in the presence of air. There have been reports of thiophene, phenyl, or other conjugated functional group substituted anthracene, tetracene, and pentacenes, that show good electronic properties (see Anthony, J. E., *Chemical Reviews* (2006), 106(12), 5028-5048, Functionalized Acenes and Heteroacenes for Organic Electronics; Anthony, J. E., *Angewandte Chemie, Int. Ed.*, (2008), 47(3), 452-483, The Larger Acenes: Versatile Organic Semiconductors; Hong M., et al., *J. Am. Chem. Soc.*, (2006), 128(29), 9304-9305, 2,6-Bis[2-(4-pentylphenyl)vinyl]anthracene: A Stable and High Charge Mobility Organic Semiconductor with Densely Packed Crystal Structure; Klauk, H., et al., *Advanced Materials*, (2007), 19(22), 3882-3887, Organic Transistors Based on Di(phenylvinyl)anthracene: Performance and Stability; Hong M., et al., *J. Am. Chem. Soc.*, (2005), 127(8), 2406-2407, High-Performance, Stable Organic Thin-Film Field-Effect Transistors Based on Bis-5'-alkylthiophen-2'-yl-2,6-anthracene Semiconductors). For example, single crystals of 5,6,11,12-tetraphenyltetracene show a much higher mobility than those of tetracene and pentacene (Anthony, J. E., *Angewandte Chemie, Int. Ed.*, (2008), supra). However, the synthesis of these conjugated small molecules is not simple. The addition of these conjugated substituents onto structures, which already have some degree of electronic activity, has generally resulted in a further enhancement of the electronic activity.

Several examples of α-, α'-substituted FT3 have been reported for potential applications as organic light-emitting transistors (OLETs) (see for example, Cicoira, F., et al., *Advanced Materials*, (2006), 18(2), 169-174, Organic Light-Emitting Transistors Based on Solution-Cast and Vacuum-Sublimed Films of a Rigid Core Thiophene Oligomer; Sun, Y., et al., *Advanced Functional Materials* (2006), 16(3), 426-432, High-Performance and Stable Organic Thin-Film Transistors Based on Fused Thiophenes), Monochromatic OLED Pixel Arrays (Viola, I., et al., *Advanced Materials*, (2007), 19(12), 1597-1602, Bicolor Pixels from a Single Active Molecular Material by Surface-Tension-Driven Deposition), and OTFTs (see for example, Holmes, A. B., et al., assigned to Cambridge Display Technology, Ltd., UK, WO 9912989 A1, Fused Thiophenes for Electronic Devices; Farrand, L. et al., EP 1275651 A2, Preparation of Thienothiophene Analogs for use as Semiconductors or Charge Transport Materials; Sun, Y., et al., *Applied Physics Letters*, (2006), 88(24), 242113/1-3, Organic Thin-Film Transistors with High Mobilities and Low Operating Voltages Based on 5,5'-Bis-biphenyl-dithieno[3,2-b:2',3'-d]thiophene Semiconductor and Polymer Gate Dielectric; Melucci, M. et al., *Chemistry—A European Journal*, (2007), 13(36), 10046-10054, Liquid-Crystalline Rigid-Core Semiconductor Oligothiophenes: Influence of Molecular Structure on Phase Behaviour and Thin-Film Properties). Surprisingly, examples of α-,β-substituted FT4, FT5, or FT6 compounds have not been reported. This may be attributable to the poor solubility of α-,β-unsubstituted FT4, FT5, and FT6 compounds which could make further structural modification difficult.

In embodiments, the disclosure provides a method for making a variety of α-, α'-substituted, β-, β'-alkyl substituted FT4 to FT7 compounds including α-, α'-conjugated functional group substituted, β-, β'-alkyl substituted FT4 to FT7 compounds. The new compounds can have application in, for example, organic electronics and like applications. In embodiments, the method includes using Stille Coupling or Suzuki Coupling for preparing three monomer unit, or higher unit polymers, containing an α-, α'-linked, β-, β'-substituted fused thiophene moiety core ranging from FT4 to FT7.

In embodiments, the compounds of the disclosure provide advantages, including for example:

the simplicity or ease with which one can synthetically manipulate or systematically change one or more of the mers or units in the polymer to produce new polymer structures having highly regular or repeat structure;

the disclosed polymer preparative methods provide additional flexibility or capability to specify the regio-regularity of the polymer structures; and the disclosed methods can be used to make known polymers (see for example commonly owned and assigned copending application U.S. Ser. No. 61/072,468,) more efficiently, such as with fewer steps and fewer reagents.

Based upon other known and related compounds and polymers, the disclosed compounds and polymers are expected to have excellent organic semiconductor properties, such as increased thermal stability and oxygen stability, and increased ease of manufacture because of increased solubility and increased synthetic efficiency, such as fewer steps.

The disclosed compounds can be prepared using established synthetic methods, for example, Stille Coupling, Suzuki Coupling, or a Grignard Coupling. Use of Suzuki Coupling to synthesize three-unit (fused thiophene units) or higher unit polymers containing an α-, α'-coupled, β-, β'-substituted fused thiophene is not believed to have been previously reported. The disclosed preparative methods can be used to prepare known fused thiophene polymers (see for example, Pan, H., et al., *J. Am. Chem. Soc.*, (2007), 129(14), 4112-4113, Low-Temperature, Solution-Processed, High-Mobility Polymer Semiconductors for Thin-Film Transistors), using for example, $FeCl_3$ oxidization.

In general, the disclosed methods provide improved preparation of semi-conducting polymers containing more than one mer or unit (i.e., conjugated unit). While some of the disclosed compounds have been previously prepared by co-polymerization, such as the above mentioned $G^1$-C-$G^1$ based copolymers, the disclosed methods provide a more convergent route to prepare the compounds using a reduced number of co-monomers, for example, where multiple units are included in a single mer or polymerizable unit. This provides more structurally uniform polymers which can provide better structural organization in electronic devices and improved electronic properties.

In embodiments, the disclosure provides improved solubility of the monomers and three-unit (or higher unit) polymers containing an α-, α'-coupled, β-, β'-substituted fused thiophene because a side-chain modification can be accomplished on any of the monomers or three-unit polymers.

In embodiments, the disclosure provides a method of making α-, α'-coupled, β-, β'-substituted fused thiophenes, including α-, α'-aromatic ring substituted, β-, β'-alkyl substituted FT4 to FT7 compounds. The general Schemes 1(a-d) illustrated below for preparing α-, α'-substituted, β-, β'-alkyl substituted FT4 and FT5 compounds are applicable to FT6, FT7, and FT8 compounds, and like compounds.

Scheme 1 (a) Synthesis of α-, α'-substituted, β-, β'-alkyl substituted FT4.

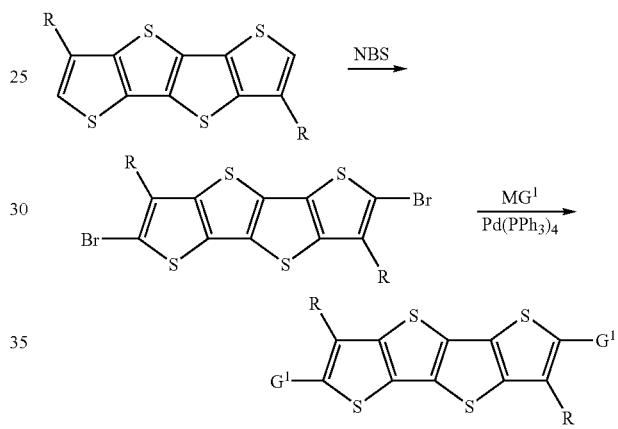

where M-$G^1$ can be, for example,

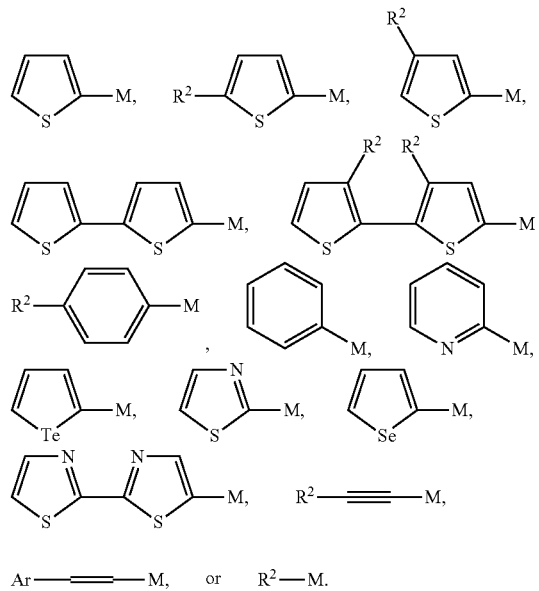

Scheme 1(b) Synthesis of α-, α'-substituted, β-, β'-alkyl substituted FT5.

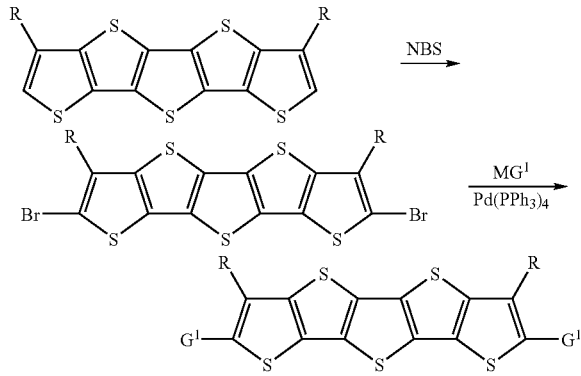

Scheme 1(c) Exemplary synthesis of three-unit polymers from α-, α'-aromatic ring substituted, β-, β'-alkyl substituted fused thiophenes FT4 and FT5.

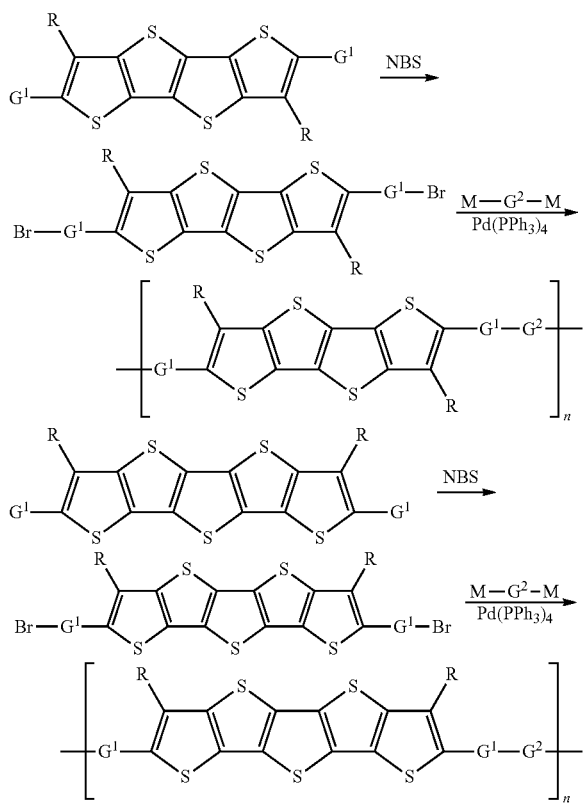

where M-G$^2$-M is as defined herein.
Scheme 1(d) Alternative exemplary syntheses of a three-unit polymer.

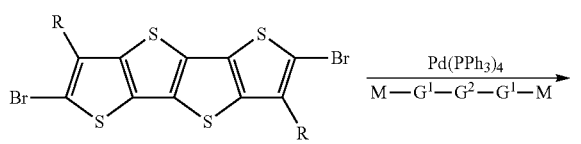

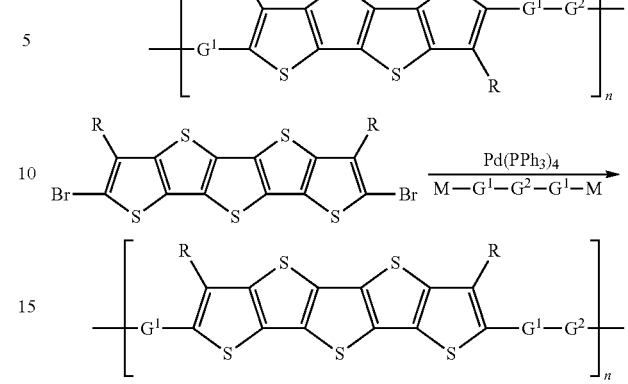

where M-G$^1$-G$^2$-G$^1$-M is as defined herein.

The syntheses of thiophene substituted FT4 (3) and FT5 (6) compounds are shown in accompanying Schemes 2(a) and 2(b), respectively. The preparative procedure begins with a dibromination reaction in the α, α'-positions of the α-, α'-unsubstituted, β-, β'-alkyl substituted fused thiophene. This can be accomplished, for example, with N-bromosuccinimide (NBS), or other like brominating agents. The resulting dibromo-FT derivatives can then be reacted with an appropriate tin reagent, for example, 2-tributyltin thiophene, and a catalyst. A variety of reagents, as shown in Scheme 1(a), can be used. While a tin reagent based Stille Coupling was demonstrated in the synthesis of these materials, other known methods to form the C—C bond, such as Suzuki Coupling, as shown in Scheme 2(c), and Grignard coupling, can be used to obtain the new compounds.

Scheme 2(a) Synthesis of α-, α'-thiophene substituted, β-, β'-alkyl substituted FT4 using Stille coupling.

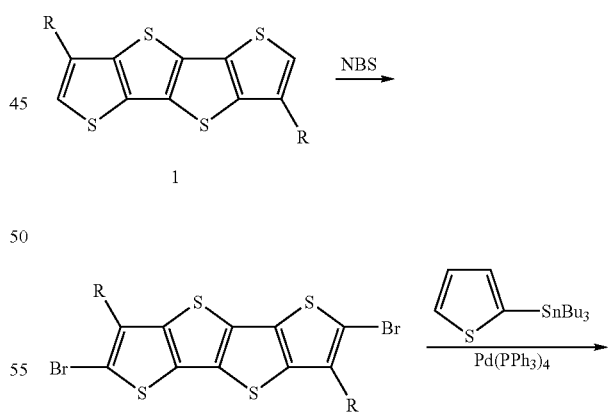

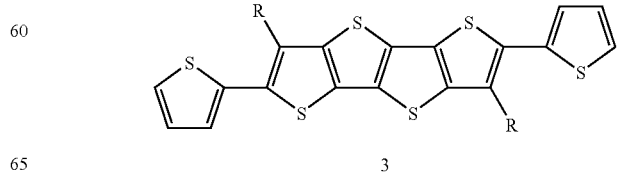

Scheme 2(b) Synthesis of α-, α'-thiophene substituted, β-, β'-alkyl substituted FT5 using Stille Coupling.

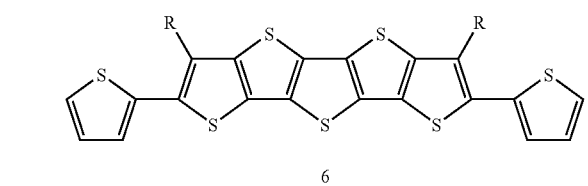

4

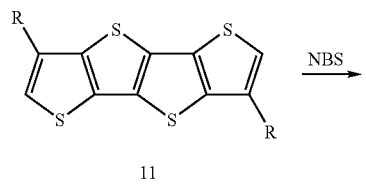

5

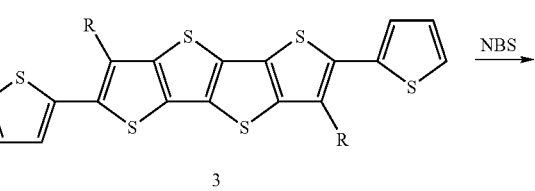

6

Scheme 2(c) Synthesis of α-, α'-p-trifluoromethylphenyl substituted, β-, β'-alkyl substituted FT5 using Suzuki coupling.

11

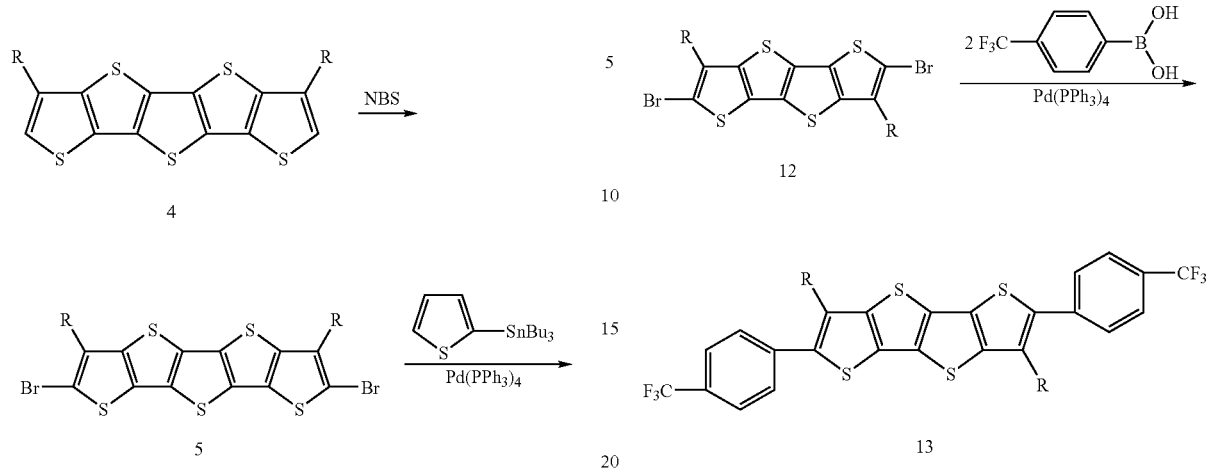

12

13

Specific examples of methods to prepare polymers based on the new compounds 3 and 6 are shown in Scheme 2(d). The first step can be, for example, bromination of compound 3 or compound 6 with NBS, or like agents, and combinations thereof. The brominated compounds 7 and 9 can then be reacted with a di-tin aryl or like derivative, such as 1,4-bis-trimethyltin benzene as shown, in the presence of a metal catalyst to form the polymers 8 and 10. In general, any aryl di-tin, vinyl di-tin, or acetylenic di-tin compound can be selected for use in the reaction to make the corresponding polymers. While the tin based Stille coupling polymerization was specifically demonstrated, other known metal catalyzed processes for the co-polymerization of aryl, vinyl, and acetylenic units via C—C bond formation, such as the Suzuki coupling shown in Scheme 2(c), or Grignard coupling can be used to form a variety of polymeric structures. The choice of coupling chemistry selected for a specific polymerization can be suggested or dictated by the type or types of monomers being polymerized.

Scheme 2(d) synthesis of three-unit polymers containing α-, α'-thiophene substituted, β-, β'-alkyl substituted FT4 and FT5.

3

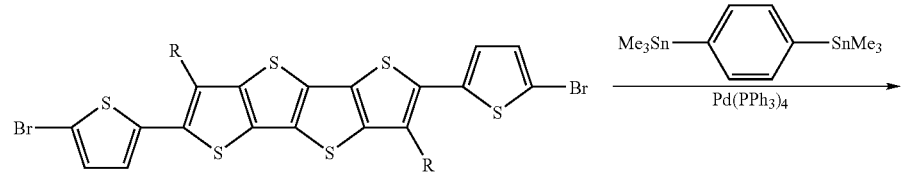

7

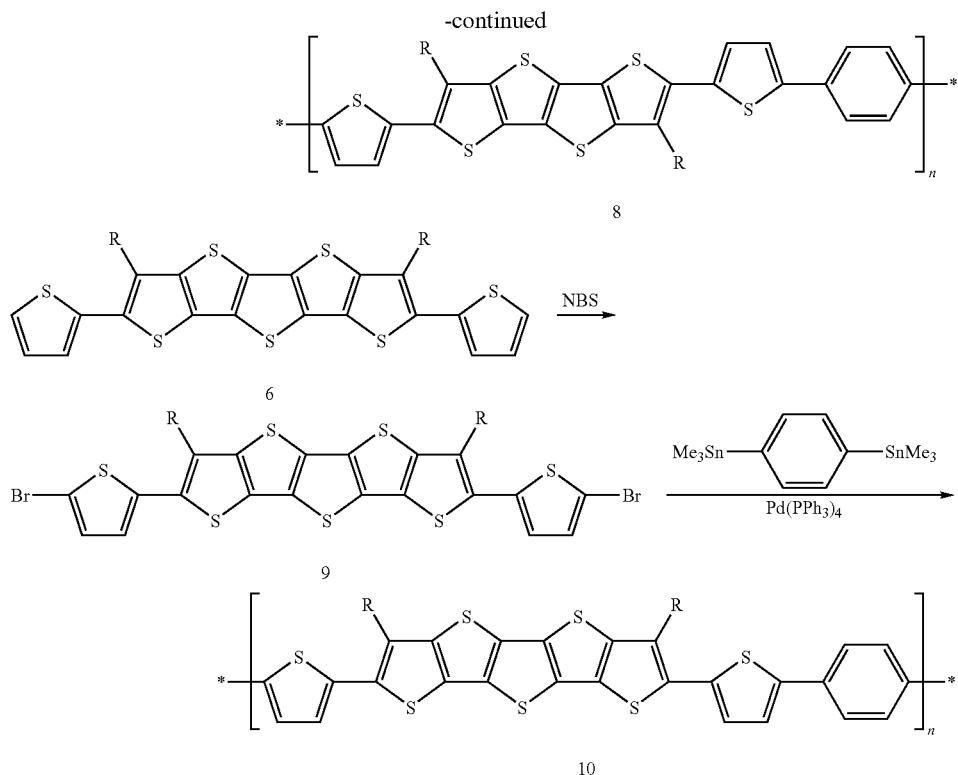

The monomer compounds of the disclosure in combination with various polymerization chemistries can provide great structural flexibility and access to numerous multi-unit polymers, for example, as illustrated in Schemes 1(c) and 1(d). The polymers shown in Scheme 1(c) consist of co-polymers made from two monomers. However, these polymers are considered to be three unit polymers having the added units $G^1$ and $G^2$ to the starting FT core, where $G^1$ and $G^2$ can be, for example, aryl, vinyl, acetylenic, or like groups. As shown in Scheme 1(d), the flexibility of the polymerization process allows for the formation of the same polymers shown in Scheme 1(c) by a different route. This alternative approach may be advantageous where a particular monomer unit is difficult to prepare or otherwise difficult to obtain. The ability of coupling chemistry to selectively place a unit in a particular position in the repeated sequence can provide polymers having more uniform two-dimensional structures compared to forming these polymers in random co-polymerization reactions. Although not limited by theory, these materials can pack more uniformly when they are assembled into electronic devices, and their semi-conducting properties can be enhanced compared to the more random polymer structures. We have unexpectedly discovered that certain fused thiophene compounds of the disclosure, and related compounds, can have superior, i.e., more compact, crystalline packing properties and the corresponding polymers can have superior conducting mobilities, when the compound has a $C_2$ symmetry element, where the $C_2$ symmetry element, or 180° rotational axis, is perpendicular to the plane of the fused thiophene core. In embodiments, the structure of the fused thiophene compounds having superior properties include those fused thiophenes of the formula FTx where x is even and the $C_2$ symmetry is about a rotational axis that is perpendicular to the plane of the fused thiophene core. Compounds and polymers of the disclosure having superior conducting mobility include FTx structures where x is an even integer of fused thiophene rings, such as FT4, FT6, FT8, and like structures compared to, for example, FTx structures where x is an odd integer of fused thiophene rings, such as FT5, FT7, FT9, and like structures.

The hole conducting mobility of polymer 8 shown in Scheme 2(d) was measured as described in the experimental section. A mobility of about 0.005 to about 0.01 $cm^2V^{-1}s^{-1}$ was measured and $I_{on/off}$ ratio of $10^5$ was obtained.

EXAMPLES

The following examples serve to more fully describe the manner of using the above-described disclosure, and the best modes contemplated for carrying out various aspects of the disclosure. It is understood that these examples do not limit the scope of this disclosure, but rather are presented for illustrative purposes.

Example 1

Synthesis of α-, α'-Thiophene Substituted, β-, β'-Alkyl Substituted Fused Thiophene FT4(3)

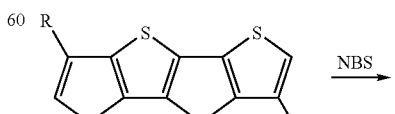

1

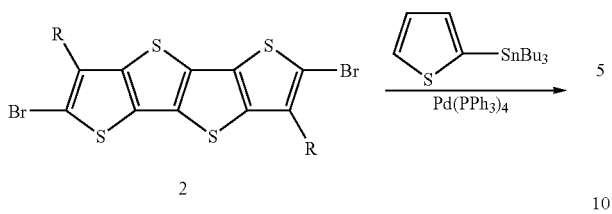

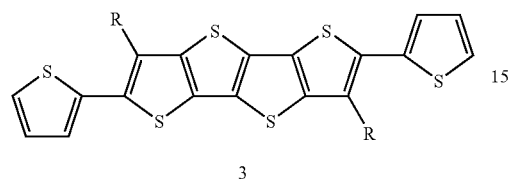

R = C₁₃H₂₇

Compound 2 (di-C13-FT4 di-bromide) was synthesized according to *J. Amer. Chem. Soc.,* 2008, 130, 13202-13203. To 0.58 g of compound 2 (0.75 mmol) in a microwave reaction test tube fitted with a stir bar, 0.62 g (1.65 mmol) of 2-thioenyl tri-n-butyltin, i.e., M-G[1], was added. This tube was flushed through by nitrogen for several minutes, sealed, and place in a glovebox. 0.250 g (0.216 mmol) of Pd(PPh$_3$)$_4$ and 9 mL of toluene were added to the tube. This tube was again sealed and placed into the microwave reactor. After 40 minutes at 120° C. in the reactor, the reaction mixture was purified by short-path silica gel column chromatography, using hot hexane as the elutant. Under reduced pressure, the hexane solvent was removed to yield an oily product to which about 100 mL of a methanol/ethanol (1:1) (v:v) mixture was added to yield 3 as a yellow precipitate. The precipitate was collected by filtration and dried under vacuum (0.49 g, 84% yield). $^1$H NMR (300 MHz, CD$_2$Cl$_2$): δ 7.40 (d, J=5.1 Hz, 2H), 7.22 (d, J=3.3 Hz, 2H), 7.12 (br t, J=4.5 Hz, 2H), 2.93 (t, J=7.8 Hz, 4H), 1.79 (p, J=7.5 Hz, 4H), 1.51-1.17 (m, 40H), 0.87 (t, J=6.6 Hz, 6H); HRMS (MALDI) m/z calcd for [C$_{44}$H$_{60}$S$_6$] 780.2967, found 780.30193.

Synthesis of α-, α'-Thiophene Substituted, β-, β'-Alkyl Substituted Fused Thiophenes FT5 (6).

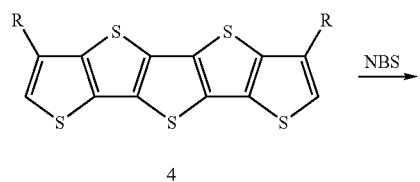

Compound 5 (di-C13-FT5 di-bromide) was synthesized according to *J. Amer. Chem. Soc.,* 2008, 130, 13202-13203. To 0.99 g of compound 5 (1.19 mmol) in a microwave reaction test tube fitted with a stir bar, 0.93 g (2.50 mmol) of 2-thioenyl tri-n-butyltin was added. This tube was flushed with nitrogen for several minutes, sealed, and placed into a glove box. 0.413 g (0.357 mmol) of Pd(PPh$_3$)$_4$ and 12 mL of toluene were added to the tube. This tube was again sealed and placed into a microwave reactor. After 40 minutes at 120° C. in the reactor, the reaction mixture was purified by short-path silica gel column chromatography, using hexane as the elutant. Under reduced pressure, the hexane solvent was removed to yield an oily product to which about 100 mL of a methanol/ethanol (1:1) mixture was added to yield 6 as a yellow precipitate. The yellow precipitate was collected by filtration and dried under vacuum (0.91 g, 91% yield). $^1$H NMR (300 MHz, CD$_2$Cl$_2$): δ 7.41 (d, J=4.2 Hz, 2H), 7.22 (d, J=3.6 Hz, 2H), 7.12 (br t, J=4.0 Hz, 2 H), 2.94 (t, J=7.8 Hz, 4H), 1.79 (p, J=7.5 Hz, 4H), 1.52-1.18 (m, 40H), 0.87 (t, J=6.6 Hz, 6H); HRMS (MALDI) m/z calcd for [C$_{46}$H$_{60}$S$_7$] 836.2711, found 836.274.

Example 2

Synthesis of Three-Unit Polymer 8 from of α-, α'-Thiophene Substituted, β-, β'-Alkyl Substituted Fused Thiophene FT4 (7)

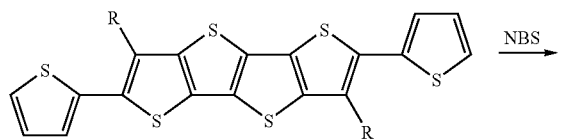

-continued

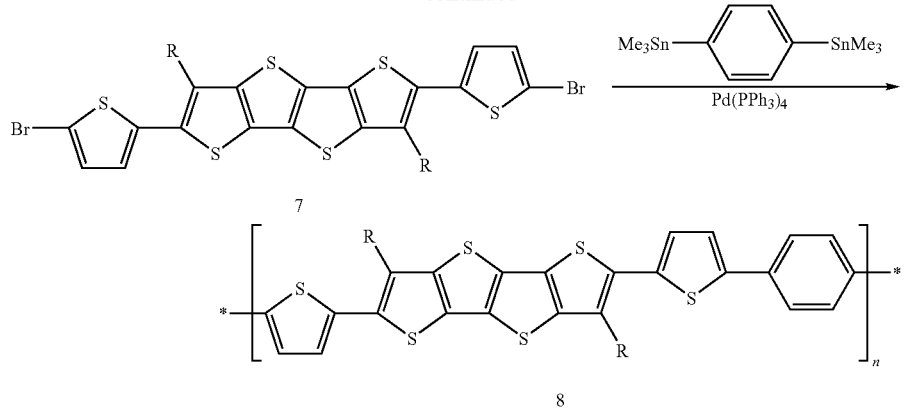

7

8

To a stirred solution of compound 3 (0.44 g, 0.56 mmol) in methylene chloride (30 mL) in a flask was added dropwise, a solution of N-bromo succinimide (NBS) (0.21 g, 1.17 mmol) in DMF (15 mL). The resulting mixture was stirred in darkness for 48 hrs. Methylene chloride was removed with a rotary evaporator. The solid residue was washed with water (3×100 mL) and methanol (50 mL). Solid was then dried and re-crystallized from hexane to give 0.33 grams of compound 7 (62% yield). $^1$H NMR (300 MHz, CD$_2$Cl$_2$): δ 7.07 (d, J=3.6 Hz, 2H), 6.95 (d, J=3.3 Hz, 2H), 2.89 (t, J=4.5 Hz, 4H), 1.77 (p, J=6.9 Hz, 4H), 1.51-1.18 (m, 40H), 0.87 (t, J=6.8 Hz, 6H); HRMS (MALDI) m/z calcd for [C$_{44}$H$_{58}$Br$_2$S$_6$] 936.1259, found 936.1230.

chloric acid (5 mL) solution and then stirred for 16 hrs at ambient temperature. The resulting precipitate was filtered and extracted in a Soxhlet apparatus for 24 h with acetone and for 24 h with hexane. The obtained polymer was then dissolved into 1,2-chlorobenzene and filtered, and then precipitated in methanol. The collected polymer product 8 was dried in vacuum to 0.13 grams (45% yield). GPC (1,2-dichlorobenzene, polystyrene standards) M$_n$ 14,418, M$_w$ 20,856.

Synthesis of three-unit polymer 10 from of α-, α'-thiophene substituted, β-, β'-alkyl substituted fused thiophene FT5 (9)

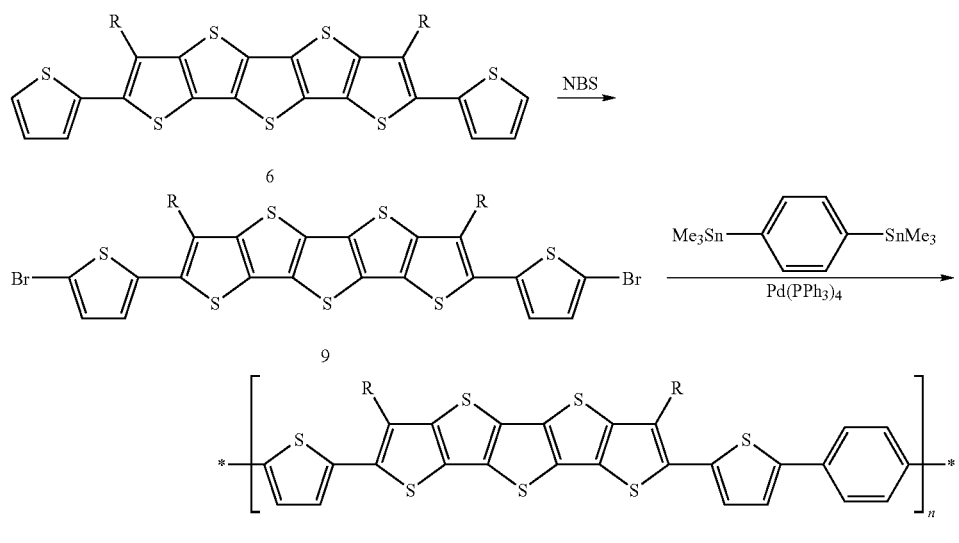

6

9

10

Three-unit polymer 8 containing α-, α'-thiophene substituted, β-, β'-alkyl substituted FT4. Compound 7 (0.32 g, 0.34 mmol) and 1,4-phenylenebis (trimethylstannane) (0.14 g, 0.34 mmol), i.e. M-G'-M, were transferred into a three neck flask fitted with a stir bar. Nitrogen was passed through the flask for five minutes. The flask was sealed and placed in a glove box. To the flask were added 0.040 g (0.0341 mmol) of Pd(PPh$_3$)$_4$ and 25 mL of toluene. This flask was heated to 120-130° C. under nitrogen for 16 hrs before being poured into a mixture of methanol (200 mL) and concentrated hydro- To a stirred solution of compound 6 (0.52 g, 0.62 mmol) in methylene chloride (130 mL) in a flask, was added dropwise a solution of N-bromo succinimide (NBS) (0.23 g, 1.30 mmol) in DMF (60 mL). The resulting mixture was stirred in darkness for 48 hrs.

Methylene chloride was then removed with a rotary evaporator. The remaining solid residue was washed serially with water (3×100 mL), methanol (50 mL), and ethanol (50 mL). This solid was re-crystallized from hexane to give 0.58 grams of compound 9 (94% yield). $^1$H NMR (300 MHz, CD$_2$Cl$_2$): δ

7.09 (d, J=3.9 Hz, 2H), 6.95 (d, J=3.9 Hz, 2H), 2.90 (t, J=7.8 Hz, 4H), 1.78 (p, J=7.5 Hz, 4H), 1.52-1.18 (m, 40 H), 0.87 (t, J=6.9 Hz, 6H); HRMS (MALDI) m/z calcd for [$C_{46}H_{58}Br_2S_7$] 992.1007, found 992.095.

Three-unit polymer 10 containing α-, α'-thiophene substituted, β-, β'-alkyl substituted thiophene FT5. Compound 9 (0.58 g, 0.58 mmol) and 1,4-phenylenebis(trimethylstannane) (0.24 g, 0.58 mmol) were placed in a three neck flask fitted with a stir bar. Nitrogen was passed through the flask for five minutes. The flask was sealed and was placed in a glove box. To the flask were added 0.067 g (0.058 mmol) of Pd(PPh$_3$)$_4$ and 25 mL of toluene. The flask was heated to 120-130° C. under nitrogen for 16 hrs and then poured into a mixture of methanol (400 mL) and concentrated hydrochloric acid (5 mL) and stirred 16 hrs at ambient temperature. The precipitate was filtered and extracted in a Soxhlet apparatus for 24 hrs with acetone and then for 24 hrs with hexane. The remaining solid was then dissolved into 1,2-chlorobenzene, filtered, and precipitated in methanol. The collected polymer was dried in vacuum to 0.47 grams (88% yield). GPC (1,2-dichlorobenzene, polystyrene standards) $M_n$ 8,759, $M_w$ 10,792.

Example 3

Synthesis of α-, α'-Trifluoromethylphenyl Substituted, β-, β'-Alkyl Substituted Fused Thiophenes FT4 (13)

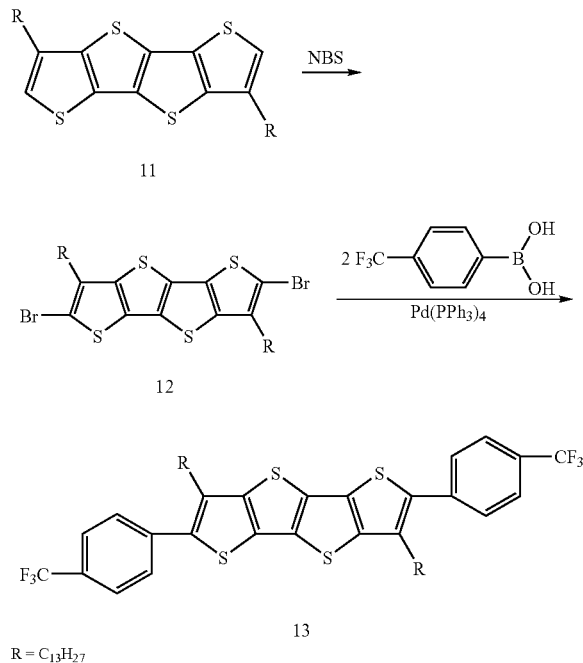

R = $C_{13}H_{27}$

Compound 12 was synthesized according to *J. Amer. Chem. Soc.*, 2008, 130, 13202-13203. To 0.69 g of compound 12 (0.78 mmol) in a microwave reaction test tube fitted with a stir bar, 0.37 g (1.95 mmol) of 4-(trifluoromethyl)phenylboronic acid was added. To this mixture, 6 mL of 20% aqueous Na$_2$CO$_3$ and 15 mL of THF were added. This tube was flushed with nitrogen for several minutes, sealed, and placed into a glove box. To the tube were added 0.135 g (0.117 mmol) of Pd(PPh$_3$)$_4$ and 2 mL of toluene. This tube was again sealed and placed into the microwave reactor. After 40 minutes at 90° C. in the reactor, the organic layer was purified by short-path silica gel column chromatography, using hexane as the elutant. Under reduced pressure, the hexane solvent was removed from the elutant to yield an oily product to which about 100 mL of a methanol/ethanol (1:1) mixture was added to yield 13 as a yellow precipitate. The yellow precipitate was collected by filtration and dried under vacuum (0.57 g, 72% yield). $^1$H NMR (300 MHz, CD$_2$Cl$_2$): δ 7.70 (AA'BB', 8H), 2.86 (t, J=4.5 Hz, 4H), 1.79 (p, J=4.9 Hz, 4H), 1.54-1.19 (m, 56H), 0.87 (t, J=4.7 Hz, 6H).

Example 4

Device fabrication and characterization All top-contact bottom-gate transistors using polymer 10 as an organic semiconducting channel were fabricated in air. Si<100> wafers were used as gate electrodes with silicon dioxide as the gate dielectric. OFET devices based on 10 in 1,2-dichlorobenzene were fabricated on the octyltrichlorosilane (C8OTS) vapor treated Si/SiO$_2$ wafers. A general procedure for preparing OFET devices and methods for measuring, for example, mobility are disclosed, for example, in *J. Amer. Chem. Soc.*, 2008, 130, 13202-13203. A representative current-voltage curve for the device of polymer 10 is shown in FIG. 1.

Example 5

Solubility of Selected FT4 And FT5 Compounds Table 1 provides a solubility comparison of some α-, α'-unsubstituted, β-, β'-alkyl substituted FT4 (and FT5), with some α-, α'-substituted, β-, β'-alkyl substituted FT4 (and FT5) compounds. General Procedure: 10 mg of a FT4 or FT5 compound was mixed with 5.0 mL of a specified solvent and then sealed in a screw-top glass vial. The resulting mixture was kept in an ultrasonic bath for 30 minutes at ambient temperature and then kept quiescent for 30 minutes to check whether a clear solution formed. If the mixture was still not clear after these 60 minutes, an additional 5.0 mL of the same solvent was added to the vial and the 60 minute mixing and standing procedure was repeated up to a total of 20 mL of solvent.

These results suggest a general solubility trend of these FT4 and FT5 compounds. FT4 and FT5 compounds have a solubility trend of: toluene>CH$_2$Cl$_2$>hexane. α-, α'-substituted, DC13 (R=C$_{13}$H$_{37}$) FT4 compounds have better solubility than related α-, α'-substituted, DC17 (R=C$_{17}$H$_{35}$) FT4 compounds. In general, with the same alkyl side chain, the α-, α'-phenyl, β-, β'-alkyl substituted FT4 (and FT5) compounds have better solubility than α-, α'-thiophene, β-, β'-alkyl substituted FT4 (and FT5) compounds. The α-, α'-thiophene, β-, β'-alkyl substituted FT4 (and FT5) compounds have a slightly improved solubility over the α-, α'-unsubstituted parent β-, β'-alkyl substituted FT4 and FT5 compounds. With the same side chain, α-, α'-substituted, β-, β'-alkyl substituted FT5 compounds have much better solubility than the related α-, α'-substituted, β-, β'-alkyl substituted FT4 compounds.

The disclosure has been described with reference to various specific embodiments and techniques. However, it should be understood that many variations and modifications are possible while remaining within the spirit and scope of the disclosure.

TABLE 1

Solubility of Selected FT4 and FT5 Compounds.

| FT Structure | Solvent Volume (mL) | hexane | toluene | CH$_2$Cl$_2$ |
|---|---|---|---|---|
| C$_{13}$H$_{27}$ ... C$_{13}$H$_{27}$ (FT4) | 5 | − | + | 0 |
|  | 10 | − | ++ | ++ |
|  | 15 | 0 |  |  |
|  | 20 | 0 |  |  |
| C$_{13}$H$_{27}$ / thienyl substituted FT4 | 5 | − | ++ | ++ |
|  | 10 | − |  |  |
|  | 15 | 0 |  |  |
|  | 20 | 0 |  |  |
| C$_{13}$H$_{27}$ / Ph substituted FT4 | 5 | − | ++ | 0 |
|  | 10 | 0 |  | ++ |
|  | 15 | 0 |  |  |
|  | 20 | ++ |  |  |
| C$_{17}$H$_{35}$ FT4 | 5 | − | 0 | − |
|  | 10 | − | 0 | − |
|  | 15 | − | 0 | − |
|  | 20 | − | + | 0 |
| C$_{17}$H$_{35}$ / thienyl substituted FT4 | 5 | − | 0 | 0 |
|  | 10 | − | + | + |
|  | 15 | 0 | ++ | + |
|  | 20 | 0 | ++ | ++ |
| C$_{17}$H$_{35}$ / Ph substituted FT4 | 5 | − | ++ | 0 |
|  | 10 | − | ++ | + |
|  | 15 | − |  | ++ |
|  | 20 | 0 |  |  |
| C$_{13}$H$_{27}$ FT5 | 5 | 0 | ++ | + |
|  | 10 | ++ |  | ++ |
|  | 15 |  |  |  |
|  | 20 |  |  |  |
| C$_{13}$H$_{27}$ / thienyl substituted FT5 | 5 | − | ++ | ++ |
|  | 10 | − |  |  |
|  | 15 | 0 |  |  |
|  | 20 | 0 |  |  |
| C$_{13}$H$_{27}$ / Ph substituted FT5 | 5 | ++ | ++ | ++ |
|  | 10 |  |  |  |
|  | 15 |  |  |  |
|  | 20 |  |  |  |

Key:
− = insoluble
0 = partially soluble
+ = nearly all soluble; some minor residual
++ = complete solubility
open box = presumed solubility at lower concentrations

What is claimed is:

1. A fused thiophene compound of the formula:

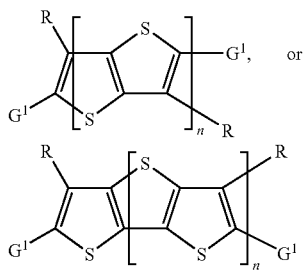

where
each R is independently a substituted or unsubstituted, $(C_{1-24})$hydrocarbyl;
n is an integer from 2 to 4; and a salt thereof, wherein each -G[1] is independently a monovalent moiety selected from

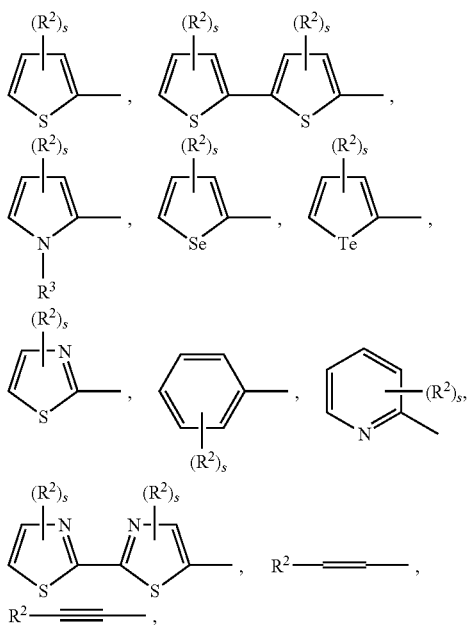

or a combination thereof,
each R[2] is independently H, or a monovalent, substituted or unsubstituted, saturated or unsaturated, $(C_{1-24})$hydrocarbyl, —Ar, —F, or a combination thereof,
s is an integer from 0 to 5.

2. A compound of the formula

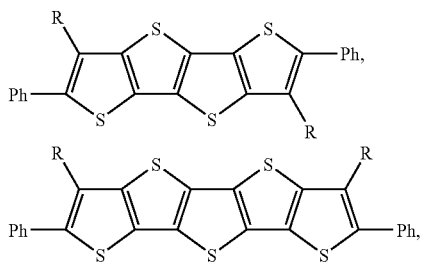

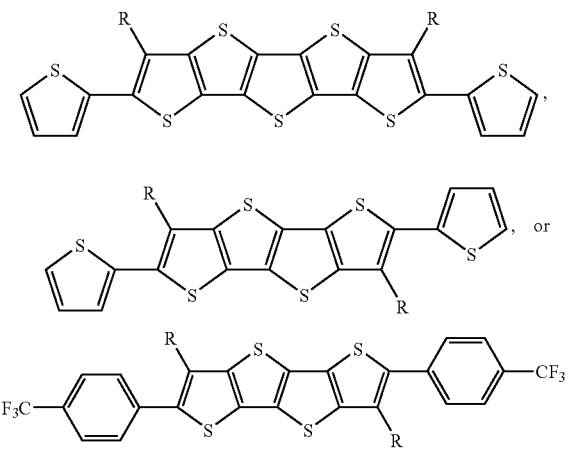

where each Ph is phenyl (—$C_6H_5$), each R is independently a substituted or unsubstituted, $(C_{1-24})$hydrocarbyl, and a salt thereof, or a mixture thereof.

3. The compound of claim 2, selected from
4,11-bis(thiophen-2-yl)-5,12-ditridecyl-3,7,10,14-tetrathiatetracyclo[6.6.0.0$^{2,6}$.0$^{9,13}$]tetradeca-1 (8),2(6),4,9(13),11-pentaene;
4,11-bis(thiophen-2-yl)-5,12-diheptadecyl-3,7,10,14-tetrathiatetracyclo[6.6.0.0$^{2,6}$.0$^{9,13}$]tetradeca-1(8),2(6),4,9(13),11-pentaene;
6,14-bis(thiophen-2-yl)-5,15-ditridecyl-3,7,10,13,17-pentathiapentacyclo[9.6.0.0$^{2,9}$.0$^{4,8}$.0$^{12,16}$]heptadeca-1 (11),2(9),4(8),5,12(16),14-hexaene;
4,11-diphenyl-5,12-ditridecyl-3,7,10,14-tetrathiatetracyclo[6.6.0.0$^{2,6}$.0$^{9,13}$]tetradeca-1(8),2(6),4,9(13),11-pentaene;
6,14-diphenyl-5,15-ditridecyl-3,7,10,13,17-pentathiapentacyclo[9.6.0.0$^{2,9}$.0$^{4,8}$.0$^{12,16}$]heptadeca-1(11),2(9),4(8),5,12(16),14-hexaene;
4,11-bis(4-trifluoromethylphenyl)-5,12-diheptadecyl-3,7,10,14-tetrathiatetracyclo[6.6.0.0$^{2,6}$.0$^{9,13}$]tetradeca-1 (8),2(6),4,9(13),11-pentaene; or
4,11-diphenyl-5,12-diheptadecyl-3,7,10,14-tetrathiatetracyclo[6.6.0.0$^{2,6}$.0$^{9,13}$]tetradeca-1(8),2(6),4,9(13),11-pentaene;
and a salt thereof, or a mixture thereof.

4. A method for making a compound of claim 1 of the formula:

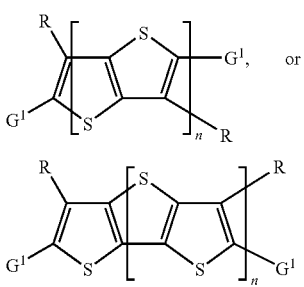

comprising:

contacting a core compound of the formula:

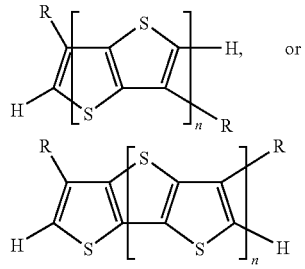

with an halogenating agent to form the α-, α'-, dihalogenated product of the formula X—C—X where X is halogen, and C is the contacted core compound; and contacting the X—C—X product with at least two mole ratio equivalents of a coupling compound of the formula M-G$^1$ and a metal catalyst to form the α-, α'-, disubstituted product of the formula G$^1$-C-G$^1$.

5. The method of claim 4 wherein the coupling compound of the formula M-G$^1$ comprises an M having an —SnR$^4{}_3$, —B(OH)$_2$, —B(OR$^4$)$_2$, —B(cyclo-OR$^4$O—), or —MgX, or a combination thereof, where X is halogen, each R$^4$ is independently a monovalent, substituted or unsubstituted, (C$_{1-24}$)hydrocarbyl, and -G$^1$ is a monovalent moiety selected from

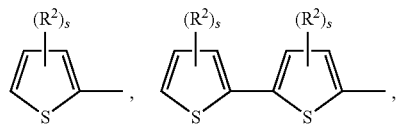

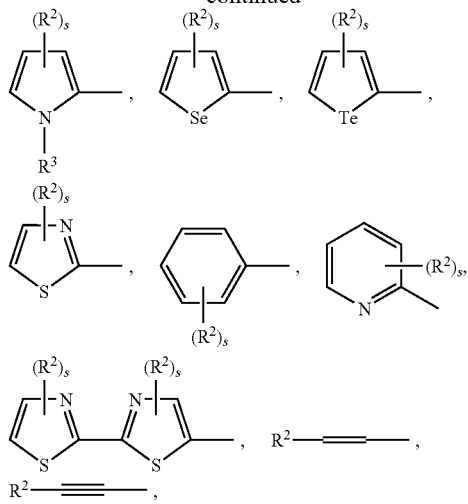

or a combination thereof, each R$^2$ is independently H, or a monovalent, substituted or unsubstituted, saturated or unsaturated, (C$_{1-24}$)hydrocarbyl, —Ar, —F, or a combination thereof, R$^3$ is H, or a monovalent, substituted or unsubstituted, saturated or unsaturated, (C$_{1-24}$)hydrocarbyl, and s is an integer from 0 to 5.

6. The compound of claim 3 wherein the solubility in an organic solvent is from about 1 to about 100 mg per milliliters.

7. The compound of claim 3 wherein the solubility in an organic solvent is from about 1 to about 10 mg per milliliters.

8. The compound of claim 6 wherein the organic solvent is toluene, methylene chloride, hexane, or a mixture thereof.

* * * * *